(12) United States Patent
White et al.

(10) Patent No.: US 6,482,404 B1
(45) Date of Patent: Nov. 19, 2002

(54) TRANSPLANTATION OF TISSUE COMPRISING A DNA SEQUENCE ENCODING A HOMOLOGOUS COMPLEMENT RESTRICTION FACTOR

(76) Inventors: David James White, 67 London Road, Harston, Cambridge (GB), CB2 5QJ; Alan Frederick Williams, 326 Oxford Road, Kidlington (GB), OX5 1DA ( * ) Notice: Subject to any disclaimer, the term of this patent is extended or adjusted under 35 U.S.C. 154(b) by 0 days.

(21) Appl. No.: 08/464,129

(22) Filed: Jun. 5, 1995

Related U.S. Application Data

(63) Continuation of application No. 08/347,210, filed on Nov. 21, 1994.

(51) Int. Cl.[7] ........................ A01N 63/00; A61K 48/00; A01K 67/027; C12N 5/00
(52) U.S. Cl. ........................ 424/93.21; 424/9.2; 800/14; 800/17; 800/18; 435/325
(58) Field of Search ............................. 800/2, 14, 17, 800/18; 424/93.1, 93.2, 93.21; 435/325; 536/23.1

(56) References Cited

U.S. PATENT DOCUMENTS

| | | |
|---|---|---|
| 4,431,636 A | 2/1984 | Schaub et al. |
| 5,545,619 A | 8/1996 | Atkinson et al. |
| 5,679,546 A | 10/1997 | Ko et al. |

FOREIGN PATENT DOCUMENTS

| | | | |
|---|---|---|---|
| EP | 0222661 | | 5/1987 |
| EP | 0244267 | | 11/1987 |
| EP | 358 130 | | 3/1990 |
| WO | WO 8800239 | | 1/1988 |
| WO | WO 8901041 | | 2/1989 |
| WO | WO89/01041 | | 2/1989 |
| WO | WO89/61041 | * | 2/1989 |
| WO | WO89/09220 | | 10/1989 |
| WO | WO 8909220 | | 10/1989 |

OTHER PUBLICATIONS

Arnold et al (1988) Proced. Natl. Acad. Sci. 85, 2269–2273.*
Lubin D.M. and Atkinson J.P., Decay–Acceleration Factor and Membrane Cofactor Protein, vol. 153, pp. 122–145, (1989).
Abstract, J.Exp.Med., Lubin D.M. et al., vol. 174, No. 1, pp. 35–44 (1991).
Kappell et al (1992) Current Op. Biotech. 3, 548–553.*
Wall (1996) Theriogenology 45, 57–68.*
D.M. Lublin et al. J. Exp. med., vol. 168 (1988), pp. 181–194.
S. Miyagawa et al. Transplantation Proceedings, vol. 21, No. 1, pp. 520–521 (1989).
M.E. Medof et al. Chemical Abstracts, vol. 102, No. 7, p. 455, Abstract 60491v (1985).
Schilling et al., Surgery, Gynecology and Obstetrics vol. 142: 29–32 (1976).
Miyagawa et al., Transplantation, vol. 46 (6) 825–830 (1988).
Medof et al., Proc. Natl. Acad. Sci. USA vol. 84:2007–2011 (1987).
Calne, Transplant Proc. vol. II, No. 4: pp. 550–553 (1970).
Rey–Campos et al., J. Exp. Med. vol. 166 246–252 (1987).
Rey–Campos et al., J. Exp. Med. vol. 167 664–669 (1988).
Heron, Acta Pathol. Mictobiol. Scand. vol. 79 366–372 (1971).
Arnold et al., Proc. Natl. Acad. Sci. USA vol. 85:2269–2273 (1988).
Burke et al., Science vol. 236:806–812 (1987).
Berden et al., Eur. J. Immunol. vol. 8:158–162 (1978).
Medof et al. (1985) Proc. Natl. Acad. Sci. USA 82: 2980–2984.
Medof et al. (1984) J. Exp. Med., 160: 1558–1578.
Wang et al. (1991) Scand. J. Immunol., 34: 771–778.
Bouwman et al. (1990) Transplantation Proceedings, 22(3): 1063–1064.
Pruitt et al. (1991) Transplantation, 52(5): 868–873.
Marboe et al. (1990) Progress in Cardiovascular Diseases, vol. XXXII, No. 6: 419–432.
Hasan et al. (1992) Transplantation, 54(3): 408–413.
Forty et al. (1992) Transplantation Proceedings, 24(2): 488–489.
Schilling et al. (1976) Surgery, Gynecology & Obstetrics, 142: 29–32.
Miyagawa et al. (1988) Transplantation, 40(6):825–830.
Miyagawa et al. (1989) Transplantation Proceedings, 21(1): 520–521.
Platts–Mills and Ishizaka (1974) The Journal of Immunology, 113(1): 348–358.
Edwards (1981) Trasplantation, 31(3): 226–227.
Atkinson and Farries (1987) Immunology Today, 8(7 & 8): 212–215.
Seya et al. (1988) J. Immunol., 18: 1289–1294.
Schonermark et al. (1988) Immunology, 63: 585–590.

(List continued on next page.)

Primary Examiner—Deborah Crouch
(74) Attorney, Agent, or Firm—Diane E. Furman; Thomas R. Savitsky; Hesna J. Pfeiffer

(57) ABSTRACT

Conventionally, animal tissue from one species can only be transplanted into another species when the species are concordant; otherwise, hyperimmune rejection ensues. In this invention, donor tissue is modified, for example by being transgenic, to express or otherwise be in association with one or more substances, referred to as homologous complement restriction factors (HCRFs), which are active in the recipient species to prevent the complete activation of complement and therefore rejection. The invention is in part based on the discovery that the alternative pathway of complement activation, rather than the classical pathway, is responsible for hyperacute discordant xenograft rejection.

29 Claims, 12 Drawing Sheets

OTHER PUBLICATIONS

Chartrand et al. (1979) Immunology, 38: 245–248.
Seya et al. (1986) J. Exp. Med., 163: 837–855.
White (1992) Int. Arch. Allergy Immunol., 98: 1–5.
Weis et al. (1986) Journal of Immunological Methods, 92: 79–87.
Frels et al. (1985) Science, 228: 577–580.
Yamamura et al. (1985) Nature, 316: 67–69.
Greaves et al. (1989) Cell, 56: 979–986.
Miller et al. (1989) Journal of Endocrinology, 120: 481–488.
Davis et al. (1989) J. Exp. Med., 170: 637–654.
Sugita (1988) J. Biochem, (Tokyo), 104(4):633–637 (English language abstract).
Chart showing classical and alternative pathways of complement activation (citation unknown).

* cited by examiner 3.15

3.35

3.55

4.15

4.25

```
                              SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CCACAGGTGT AACATTGTGT                                                    20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GAGATAGTGT GATCTGAGGC                                                    20
```

TRANSPLANTATION OF TISSUE COMPRISING A DNA SEQUENCE ENCODING A HOMOLOGOUS COMPLEMENT RESTRICTION FACTOR

This application is a continuation of application Ser. No. 08/347,210, filed Nov. 21, 1994 which claims priority under 35 USC 119 to PCT/GB90/01575, filed Oct. 12, 1990, GB 8922987.6, filed Oct. 12, 1989 and GB 9017198.4, filed Aug. 6, 1990.

This invention relates to biologically compatible material for use in transplants, and to the production and use of such material.

The replacement of failed or faulty animal (particularly human) tissue, including organs, has over the last four decades become a common place therapy in clinical medicine. These replacement therapies range for example from the use of the polyethylene terephthalate sold under the trade mark DACRON by DuPont to repair faulty blood vessels to the use of saphenous vein as an autograft to by-pass blocked arteries and to the transplantation from one human to another of a heart.

Organ transplantation has undergone significant development with modern immunosuppressants allowing high success rates to be achieved at relatively modest cost. The demand for organ transplantation has increased rapidly. There are now more than 20,000 organ transplants per annum carried out worldwide. This, however, represents only approximately 15% of the need as assessed by current criteria. The supply/demand ratio of donor organs of all types can not be met from existing sources. This is perhaps best illustrated with the demand for heart transplantation. The first heart transplantation by Barnard in 1967 generated considerable press coverage. Within a year, 101 heart transplants had been performed in 22 countries by 64 different surgical teams. Disillusionment followed the poor results obtained so that by the early 1970s fewer than 30 transplants per year were being performed worldwide. The introduction of cyclosporin immuno-suppression, however, has revolutionarised heart transplantation so that most centres can now anticipate success rates for heart transplantation of more than 80% one year graft (and patient survival). As expertise is gained, this survival rate can reasonably be expected to increase further. The success of this procedure, of course, fuels demand so that the medical profession and the general public become more aware that heart transplantation offers a real alternative to death, so more and more patients are referred for the procedure. Currently, over 2,000 heart transplants per annum are performed.

Today, the greatest risk of death in heart transplantation is while waiting for a suitable donor organ to become available. While the artificial heart offers a short-term support device for these patients, long-term demands are for more heart transplant centres and a greater donor supply. The potential number of individuals who might benefit from cardiac transplantation has never been scientifically established, but published estimates of the need for heart transplantation have ranged widely between 50 and 250 people per million per year depending on selection criteria, age of recipient, disease and so forth. Whatever the actual figure may be, it is quite clear already that current donor supply options are incapable of meeting demand. Similar comments can be made for kidney and liver transplantation, and it seems likely that once pancreas or Islet of Langerhans cell transplantation becomes a widely-accepted therapeutic procedure for the treatment of diabetes, shortage of this tissue will also become a prime concern.

There are further disadvantages with current transplantation therapy. It is by no means always the case that donor organs are fit for use in transplantation, not least because many organ donors are themselves victims of some accident (for example, a road accident) which has caused death by injury to some organ other than that which is being transplanted; however, there may be some additional injury to or associated difficulty with the organ to be transplanted.

Further, because of the unpredictable availability of organs from donors, transplant surgery often can not be scheduled as a routine operation involving theatre time booked some while in advance. All too frequently, surgical teams and hospital administrators have to react the moment a donor organ is identified and work unsocial hours, thereby adding to administrative and personal difficulties.

In the case of heart, liver and lung transplants, if rejection is encountered it will not usually be possible to retransplant unless by chance another suitable donor becomes available within a short space of time.

Apart from the above medical difficulties, current transplantation practice can in some cases involve social difficulties. In the first place, there may be religious objections to removing organs from potential donors, particularly in cultures believing in reincarnation. There are of course other ethical and social difficulties encountered in removing organs from dead humans, particularly as consent is required in some countries. Finally, the appearance of a commercial trade in live kidney donors is causing concern, particularly in certain third world countries, and it would be socially desirable to suppress or reduce such a trade.

Conventional transplantation surgery, as outlined above with its disadvantages, involves the transplantation from one animal of a particular species (generally human) to another of the same species. Such transplantations are termed allografts. Because of the difficulties with conventional allograft supply, as outlined above, attention has focused on the possibility of using xenografts in transplantation. Xenografting is the generic term commonly used for the implantation of tissues, including cells and organs, across species barriers.

There have already been several examples of the successful use of xenografts in therapeutic replacement schedules. For example, recent years have witnessed the use of pig tissue for aortic valve replacement, pig skin to cover patients with severe burns, and cow umbilical vein as a replacement vein graft. All of these xenografts have, however, one point in common: they provide a mechanical replacement only. The tissue used is biologically non-functional. The reason for this is that the immune processes existing in man immediately (within minutes or hours) destroy the cellular integrity of tissues from most species. Such xenografts are known as discordant xenografts.

The ferocity of this destruction is phylogenetically associated. Thus, tissue from the chimpanzee, which is a primate closely related to man, can survive in man in a much the same way as an allograft; such a xenograft is known as a concordant xenograft.

While it may be thought that concordant xenografts might provide the answer to the difficulties with allografts, in practice this is probably not the case. Chimpanzees are much smaller than man and chimpanzee organs are generally not big enough to work in man. In the case of kidneys this may be overcome by transplanting two chimpanzee kidneys to replace a failed human kidneys, but for liver and heart this is clearly not a possibility. Furthermore, chimpanzees breed slowly in nature and poorly in captivity, and the demand for chimpanzees as experimental animals (particularly in the current era of research into Acquired Immune Deficiency Syndrome (AIDS)) means that, yet again, demand is outstripping supply. Additionally, there may be some social difficulty with the public acceptance of the use of other primates as xenograft donors.

Attention has therefore refocused on discordant xenografts. It has been commonly believed that the reason why discordant xenografts fail so rapidly, is the existence in the recipient species of "naturally occurring" antibodies against as yet undefined antigens of the donor species (shons et al (*Europ. Surg. Res.* 26–36 (1973)). The antibodies are called "naturally occurring" because they are found to exist in individuals who have not had any immunological challenge from the donor species.

The rapid rejection—known as hyperacute antibody-mediated rejection—of an organ graft is well documented. In the early 1960s, when (allograft) kidney transplantation became a routine treatment, it was observed that transplanted kidneys were occasionally rejected by the recipient whilst the operation was still in progress. During a transplant operation, the kidney will as a rule become red and firm in consistency soon after the vessels of the recipient and donor are sutured together. Such transplants often produce urine almost immediately. In the form of rejection where the graft is destroyed while the patient is still on the table (hyperacute rejection) the destructive processes begin in the first few minutes or so after transplantation. When this occurs, the kidney becomes bluish and patchy and then congested. The consistency of the organ is also altered. As a rule, the graft becomes oedematous, no urine production occurs and the newly-transplanted kidney is then immediately removed. It has become clear that a humorally-mediated immunological response between preformed circulating antibodies in the recipient and antigens in the donor kidney are involved. The only way to avoid its occurrence in allografting is to check before transplantation that there are no antibodies existing in the recipient against the donor cells. With increased knowledge of testing for such antibodies (known as the cross match) it has become clear that this generalisation that antibody in the recipient reacts against antigens in the donor is not true and that hyperacute graft destruction, when it involves transplants between individuals of the same species is restricted to the existence of specific sorts of antibody known as T-warm positive cross-match; and almost certainly these antibodies belong to the IgG subclass. Furthermore, the presence of these antibodies always results from a pre-existing immunisation procedure either as a result of previous blood transfusions or as a result of pregnancy or, most commonly, as a result of a failed previous transplant.

The mechanism for hyperacute xenograft rejection has largely been thought to be much the same as the is mechanism for hyperacute allograft rejection, as outlined above. The literature on the mechanism of xenograft rejection is extensive, stretching back some 83 years. During that time, only three publications appear to have suggested a mechanism for xenograft rejection which does not involve antibodies. The suggestion was that the alternative pathway of complement activation was implicated in xenograft rejection (although not necessarily using such terminology). The suggestion first appeared in 1976 in a paper by Schilling et al (*Surgery, Gynaecology and Obstetrics* 142 29–32 (1976)). The suggestion was made again in 1988 and 1989 (the same data were published twice) by Miyagawa et al (*Transplantation* 46(6) 825–830 (1988) and *Transplantation Proceedings* 21(1) 520–521 (1989)). However, the results were not conclusive, because both these experiments suffered from substantially the same fault. The model chosen is claimed by the authors to be a xenograft model in which cross-species antibodies did not exist. However, it now appears that the assays used to detect cross-species antibodies were inadequate, and that the inferences drawn in these papers were based on inadequate data.

Most measures currently taken experimentally to avoid or reduce rejection in xenografts involve chemotherapeutically interfering with the recipient's immune system, largely on a non-specific basis for example with cyclosporin A and other immunosuppressants, by plasmaphoreses, by treatment with cobra venom factor, Staphylococcus protein A absorption of antibody and so on. This approach naturally follows from the chemotherapy that supports allografts.

This invention adopts a radically different approach: instead of non-specifically interfering with the recipient's immune system, the invention enables to co-administration of material which has the effect of the donor graft being regarded as self by certain components of the recipient's immune system. In particularly preferred embodiments, the donor tissue itself is modified to appear immunologically to the recipient to be self in certain respects.

It is has also been discovered that hyperacute xenograft rejection is not necessarily antibody-mediated. This arises from two observations. First, in the absence of antibody but the presence of complement, hyperacute rejection is observed; secondly, in the presence of antibody but the absence of complement, no hyperacute rejection is observed.

The invention is based on the discovery that complement activation is pre-eminent in the hyperacute destruction of a xenograft whether or not such activation is aided by the binding of appropriate antibody molecules. Activation of the alternative pathway of complement can be induced by a variety of cell products. These products are not restricted to foreign-invading cells such as bacteria or xenografts but exist on many cells. Thus, in principle, many cells of an individual could activate the alternative pathway of complement, causing massive auto-immune destruction. That this does not happen is due to the existence of a number of complement down-regulating proteins naturally present in serum and on the surface of cells. These molecules (referred to herein as "homologous complement restriction factors") prevent the complete activation of self complement either by the classical or alternative pathway by the products of self cells, thus preventing the auto-immune destruction of self. The functioning of such molecules is elegantly illustrated in paroxysmal nocturnal haemoglobinuria. In this disease, the membrane anchor of at least one of these molecules (decay accelerating factor) is absent. Thus, the protein is not retained in the erythrocyte cell membrane and detaches from the cell, which activates the alternative pathway of complement and is then lysed thus causing haemoglobinuria.

According to a first aspect of the present invention, there is provided a method of transplanting animal tissue into a recipient, wherein the tissue is derived from a donor of a different species from the recipient, the donor species being a discordant species with respect to the recipient, the method comprising grafting the tissue into the recipient and providing in association with the grafted tissue one or more homologous complement restriction factors active in the recipient species to prevent the complete activation of complement.

The word "tissue" as used in this specification means any biological material that is capable of being transplanted and includes organs (especially the internal vital organs such the heart, lung, liver and kidney, pancreas and thyroid) cornea, skin, blood vessels and other connective tissue, cells including blood and haematopoietic cells, Islets of Langerhans, brain cells and cells from endocrine and other organs and body fluids (such as PPF), all of which may be candidates for transplantation from one species to another.

A "discordant species" is a species a (generally vascularised) xenograft from which into the recipient would normally give rise to a hyperacute rejection, that is to say rejection within minutes or hours and not days (Calne Transplant Proc 2:550, 1970). Such hyperacute rejections will be well known to those skilled in the art, and ay take place in under 24 hours, under 6 hours or even under one hour after transplantation.

Complement and its activation are now well known, and are described in Roitt, *Essential Immunology* (Fifth Edition, 1984) Blackwell Scientific Publications, Oxford. The activity ascribed to complement (C') depends upon the operation of nine protein components (C1 to C9) acting in sequence, of which the first consists of three major sub-fractions termed C1q, C1r and C1s. Complement can be activated by the classical or alternative pathway, both of which will now be briefly described.

In the classical pathway, antibody binds to C1, whose C1s subunit acquires esterase activity and brings about the activation and transfer to sites on the membrane or immune complex of first C4 and then C2. This complex has "C3-convertase" activity and splits C3 in solution to produce a small peptide fragment C3a and a residual molecule C3b, which have quite distinct functions. C3a has anaphylatoxin activity and plays no further part in the complement amplification cascade. C3b is membrane bound and can cause immune adherence of the antigen-antibody-C3b complex, so facilitating subsequent phagocytosis.

In the alternative pathway, the C3 convertase activity is performed by C3bB, whose activation can be triggered by extrinsic agents, in particular microbial polysaccharides such as endotoxin, acting independently of antibody. The convertase is formed by the action of Factor D on a complex of C3b and Factor B. This forms a positive feedback loop, in which the product of C3 breakdown (C3b) helps form more of the cleavage enzyme.

In both the classical and alternative pathways, the C3b level is maintained by the action of a C3b inactivator (Factor I). C3b readily combines with Factor H to form a complex which is broken down by Factor I and loses its haemolytic and immune adherence properties.

The classical and alternative pathways are common after the C3 stage. C5 is split to give C5a and C5b fragments. C5a has anaphylatoxin activity and gives rise to chemotaxis of polymorphs. C5b binds as a complex with C6 and C7 to form a thermostable site on the membrane which recruits the final components C8 and C9 to generate the membrane attack complex (MAC). This is an annular structure inserted into the membrane and projecting from it, which forms a transmembrane channel fully permeable to electrolytes and water. Due to the high internal colloid osmotic pressure, there is a net influx of sodium ions and water, leading to cell lysis.

Homologous complement restriction factors (HCRFs) useful in the present invention can in general interfere with any part of the complement activation cascade. An HCRF may interfere solely with that part which constitutes the classical pathway, or solely with that part which constitutes the alternative pathway, or more usually may interfere with that part which is common to both the classical and alternative pathways. It is preferred that the HCRF regulator interfere with the common part of the pathway. The HCRF may be identical to a natural HCRF or simply have the appropriate function. Synthetic and semi-synthetic HCRFs, including those prepared by recombinant DNA technology and variants however prepared, are included within the term HCRF.

As has been mentioned above, homologous complement restriction factors are substances which regulate the action of the complement cascade in such a way as to reduce or prevent its lytic activity; they are used by the animal body to label tissue as self to avoid autoimmune reaction. In this invention it is possible in principle for the HCRF to be either membrane bound or free in serum, although in practice it will be preferred to have the HCRF being membrane bound on cells of the xenograft tissue. In this way, it is easier for the HCRF to be "in association with" the graft tissue. Preferred HCRFs include putative cell membrane factors including the C3b/C4b receptor (CR1), C3.dg receptor (CR2), decay accelerating factor (DAF), C3b Inactivator and membrane cofactor protein (MCP). Putative serum HCRFs include Factor H, decay accelerating factor (DAF) and C4 binding protein (C4bp). These HCRFs all down-regulate the activity of complement by interference at the C3 stage. Homologous restriction factor (HRF), which blocks at C8, is also a putative membrane factor.

Many, but not all, of the genes for suitable HCRFs are located in the RCA (regulator of complement activation) locus, which map to band q32 of chromosome 1 (Rey-Campos et al *J. Exp. Med.* 167 664–669 (1988)).

Although there has been some confusion with the nomenclature and location of HCRFs, the factors C4BP, CR1, DAF and Factor H are identified by Rey Campus et al (loc. cit.) and in their earlier study (*J. Exp. Med.* 166 246–252 (1987)). Membrane cofactor protein (MCP) is treated by some workers as synonymous with C4 binding protein (C4bp) and it may be that these two factors are either related or identical. Rother and Till ("The Complement System", Springer-Verlog, Berlin (1988)) review the regulatory factors of C3 convertase in section 1.2.3.2; they equate C4 binding protein (C4bp) with decay accelerating factor and Factor H with $B_1H$-protein and C3b Inactivator Accelerator. No doubt the nomenclature, localisation and characterisation of HCRFs will continue to evolve, but it is to be understood that the present invention contemplates the use of all HCRFs as suitability and preference dictate.

Other references to HCRFs are as follows:

Factor I (also previously known as C3b inactivator or KAF):

Tamura & Nelson (*J. Immunol.* 99 582–589 (1967);

Factor H: Pangburn et al (*J. Exp. Med.* 146 257–270 (1977);

C4 binding protein: Fujita et al (*J. Exp. Med.* 148 1044–1051 (1978));

DAF (also known as CD55): Nicholson-Weller et al (*J. Immunol.* 129 184 (1982));

Membrane Cofactor Protein (MCP; also known as CD46 and first described as gp45-70 and further known as gp66/56): Seya et al (*J. Exp. Med.* 163 837–855 (1986));

CR1 (also known as CD35): Medof et al, (*J. Exp. Med.* 156 1739–1754 (1982)) and Ross et al (*J. Immunol.* 129 2051–2060 (1982));

CR2 (also known as CD21, 3d/EBV receptor and p140): Iida et al (*J. Exp. Med.* 158 1021–1033 (1983)) and Weis et al (*PNAS* 81 881–885 (1984)).

The tissue distribution of some of the RCA proteins are as follows:

CR1: Membrane (limited): erythrocytes; monocytes; most B and some T cells; polymorphonuclear leukocytes; follicular-dendritic cells; glomerular podocytes;

CR2: Membrane (limited): most B cells; follicular-dendritic cells; some epithelial cells and a few T cell lines;

MCP: Membrane (wide): all peripheral blood cells (but erythrocytes); epithelial, endothelial and fibroblast cell lineages; trophoblast and sperm;

DAF: Membrane (wide): all peripheral blood cells; epithelial, endothelial and fibroblast cell lineages; trophoblast and sperm;

C4bp: Plasma: liver synthesis; and

H: Plasma: liver synthesis; fibroblast and monocyte cell lines.

As for proteins involved in homologous restriction at the level of the membrane attack complex, the use of which is also contemplated by means of the present invention, there is general agreement (but as yet no proof) in the form of a protein sequence that the following 65kDa (or thereabouts) proteins are identical:

C8 binding proteins (Schönermark et al, *J. Immunol.* 136 1772 (1986));

homologous restriction factor (HRF) (Zalman et al *Immunology* 83 6975 (1986)); and MAC-inhibiting protein (MIP) (Watts et al. (1988)).

The C8bp/HRF/MIP protein is attached to the cell surface by means of a glycolipid anchor, as are CD59 and DAF: these proteins are known to be functionally absent in paroxysmal nocturnal haemoglobinuria.

An 18–20 kDa protein is also implicated at the MAC level. The following are believed to be identical (but may not be):

P-18 (Sugita et al (*J. Biochem* 104 633 (1988)));

HRF-20 (Okada et al (*Intl. Immunol* 1 (1989)));

CO59 (Davies et al (*J. Exp. Med.* (September 1989))); and

Membrane inhibitor of reactive lysis (MIRL) (Hologuin et al *J. Clin. Invest* 84 7 (1989))).

The evidence for the putative identity of these proteins is that the protein and/or CDNA sequences for CD59 and HRF-20 are shown to be identical: probably they are the same as P-18/MIRL also. It should be noted that there is some homology of the CD59/HRF.20 sequence with that of murine LY-6 antigen, which is involved in T-cell activation (Gronx et al (*J. Immunol.* 142 3013 (1989))).

SP-40.40 is also involved in MAC regulation (Kivszbaum et al EMBO 8, 711 (1989)).

It is preferred that the HCRF interfere with complement activation at the C3 stage. MCP and DAF both block the positive feedback loop in the alternative pathway of C3 activation, and these constitute preferred HCRFs.

The HCRF is provided in association with the grafted tissue. This means that the HCRF is administered in such a way that the graft tissue is labelled as self, but other foreign material, such as invading bacteria, are not significantly so labelled. It may be possible simply to administer parenterally, but locally to the graft tissue, one or more appropriate HCRFs. However, in practice this may not be preferred because of the difficulty of causing adequate localisation of the HCRF The recipient species will primarily be human, but not exclusively. Other primates may be suitable recipients, as may any other species where the economics and ethics permit.

The donor species may be any suitable species which is different from the recipient species and which, having regard to the physiology of the recipient species is able to provide appropriate tissue for transplantation. For human recipients, it is envisaged that pig donors will be suitable, but any other species may be suitable.

According to a second aspect of the invention, there is provided graftable animal cells or tissue of a donor species, the cells or tissue being associated with one or more homologous complement restriction factors active in the intended recipient species to prevent the complete activation of complement, the donor species being a discordant species with respect to the recipient species.

According to a third aspect of the invention there is provided a transgenic animal having transplantable tissue, which does not give rise to xenograft rejection on transplantation into or exposure to the immuno system of at least one discordant species. A discordant species is one which would normally hyperacutely reject a xenograft from the animal.

The invention therefore encompasses the use of animal tissue derived from a donor species and one or more homologous complement restriction factors active in a recipient species, wherein the donor species is a discordant species in relation to the recipient species, in the preparation of tissue graftable into the recipient species.

According to a fourth aspect of the invention, there is provided a transgenic animal having cells capable of expressing a homologous complement restriction factor of another species. The homologous complement restriction factor will generally be active in a species which is discordant with respect to the species of the transgenic animal. The cells may be of one particular tissue, with preferences being as described with reference to the first aspect of the invention, or of more than one or all tissues, in which case the animal may become a donor of more than one tissue. Such a transgenic animal may be regarded as a collection of non-transformed (in the sense of non-proliferative) cells.

According to a fifth aspect of the invention, there is provided a non-transformed animal cell capable of expressing one or more homologous complement restriction factors active in a species which is discordant with respect to the animal cell.

According to a sixth aspect of the invention, there is provided recombinant DNA comprising DNA coding for at least one homologous complement restriction factor and one or more sequences to enable the coding DNA to be expressed by a non-transformed animal cell. The animal cell may be a cell of a transgenic animal genetically incorporating the construct. As an alternative, the sell may be a cultured organ or other tissue such as an Islet of Langerhans.

According to a seventh aspect of the invention, there is provided a genetic construct suitable for incorporation into the genetic material of an animal to produce a transgenic animal, the construct comprising DNA coding for at least one homologous complement restriction factor and one or more sequences to enable the coding DNA to be expressed in at least some cells of a transgenic animal genetically incorporating the construct. Such a genetic construct may be in the form of a mini chromosome known as a YAC. As above, the homologous complement restriction factor will generally be active in a species which is discordant with respect to the species of the transgenic animal.

According to a eighth aspect of the present invention, there is provided a method of preparing a transgenic animal, the method comprising incorporating into an animal's genetic material DNA coding for at least one homologous complement restriction factor and one or more sequences to enable the coding. DNA to be expressed in at least some cells of the transgenic animal.

Methods of producing transgenic animals are in general becoming more widespread, and the detailed steps to be taken may be as now conventionally used in the art. For example, WO-A-8800239 discloses the steps needed in principle to construct a transgenic animal.

The actual method of incorporation of the construct into the cells of the transgenic animal may be by micro-injection, by sperm-mediated incorporation or any other suitable method. The preliminary genetic manipulation may be carried out in a prokaryote, as is generally preferred.

DNA coding for HCRFs is either available in CDNA form or may be deduced using conventional cloning techniques. The DNA coding for decay accelerating factor (DAF) is probably the best characterised and has been described by Medof et al (*PNAS* 84 2007–2011 (1987)). A physical map of the RCA gene cluster is given in Rey-Campos et al (1988) (loc. cit. ). Variants of DAF and their preparation by recombinant DNA technology are disclosed in EP-A-0244267; such variants may be used in the present invention.

Because of the better characterisation of the genetics of DAF, and the known sequence of cDNA encoding DAF, DAF constitutes a preferred homologous complement restriction factor.

Other preferred features of the second to seventh aspects of the invention are as for the first aspect, mutatis mutandis.

The invention will now be illustrated by the following examples. In the examples, reference is made to the drawings in which.

Figure 7:
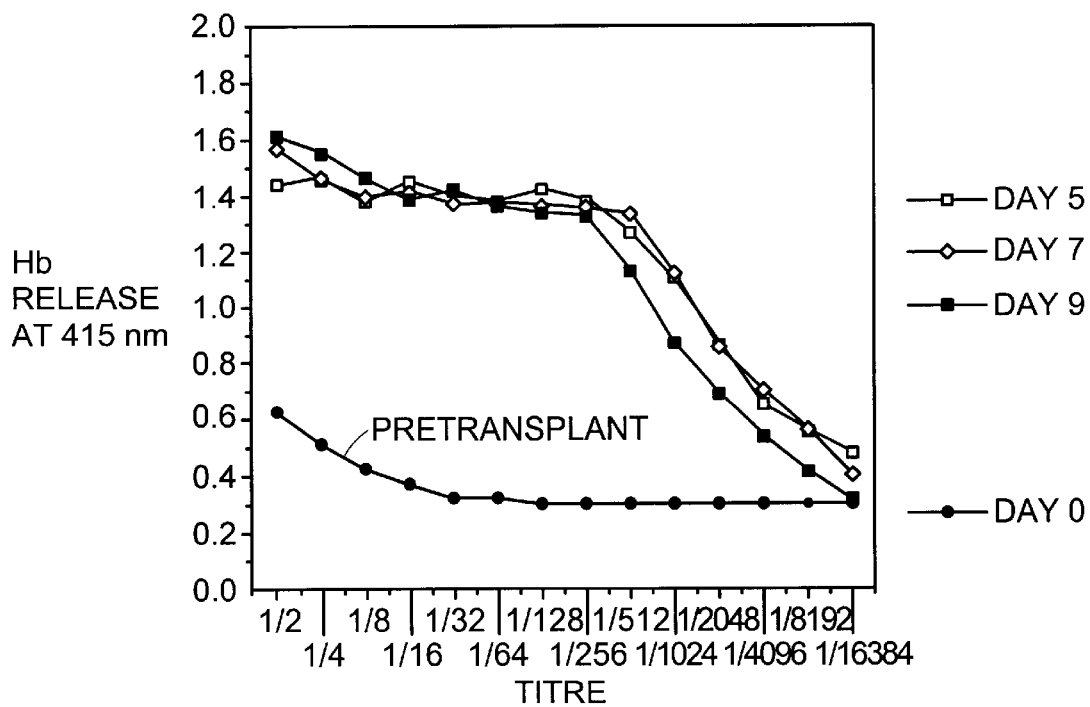
Figure 8:
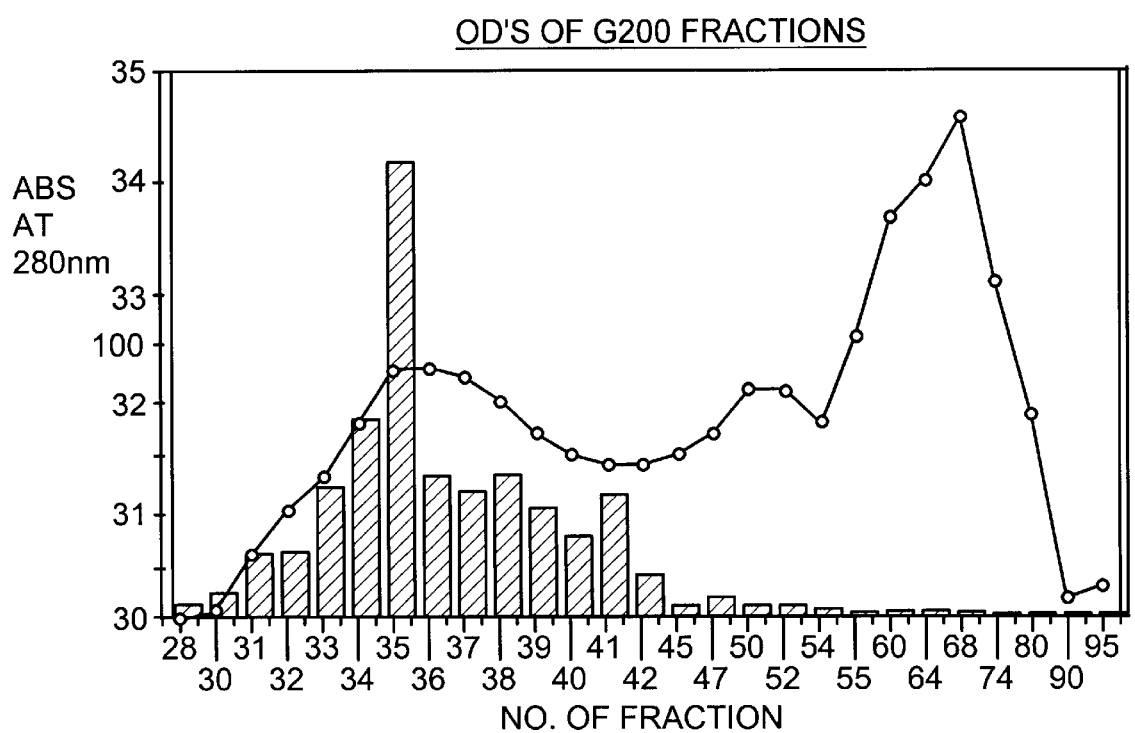
Figure 9:
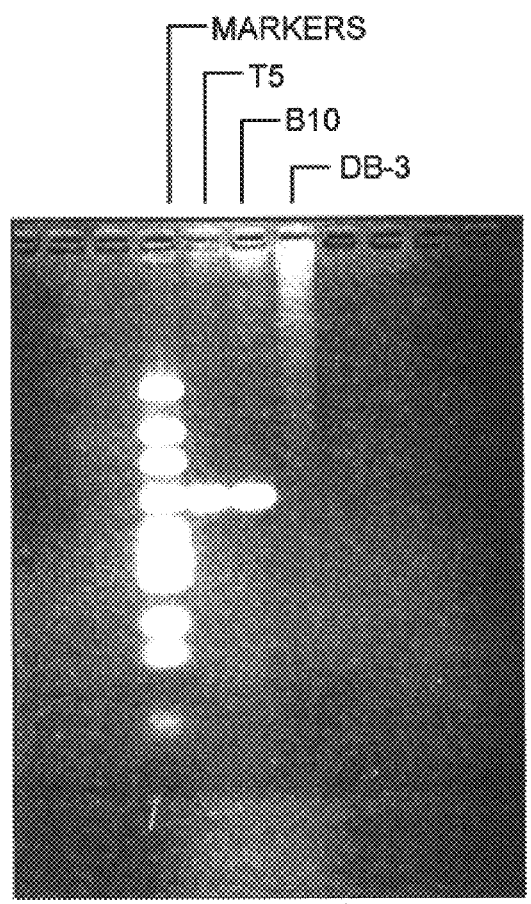
Figure 10:
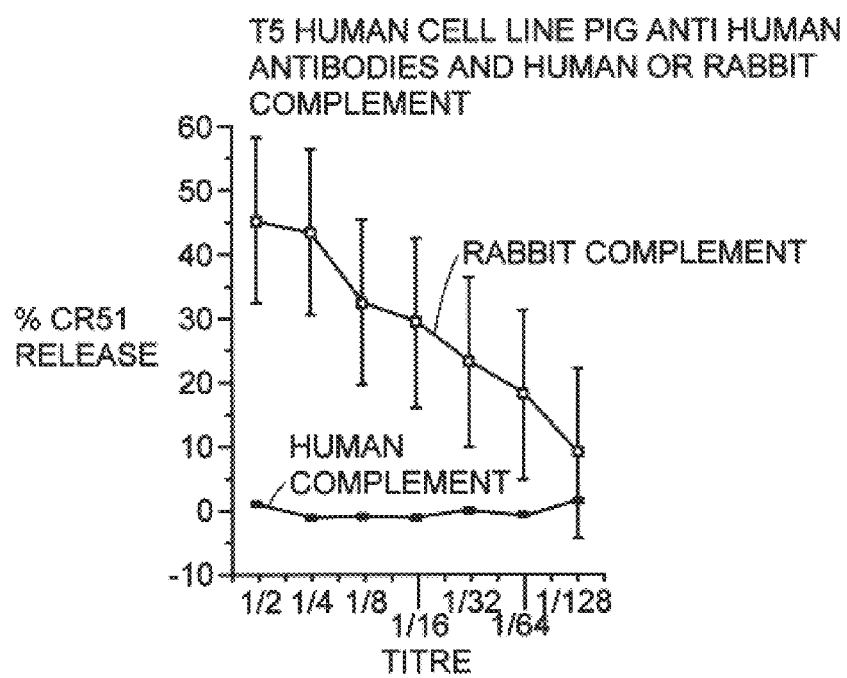
Figure 11:
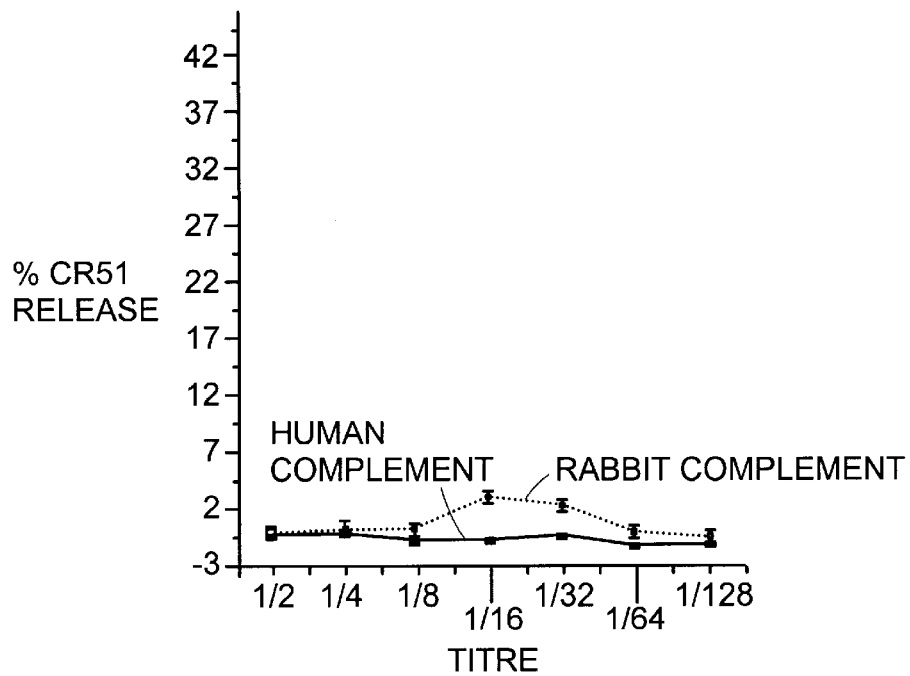
Figure 12:
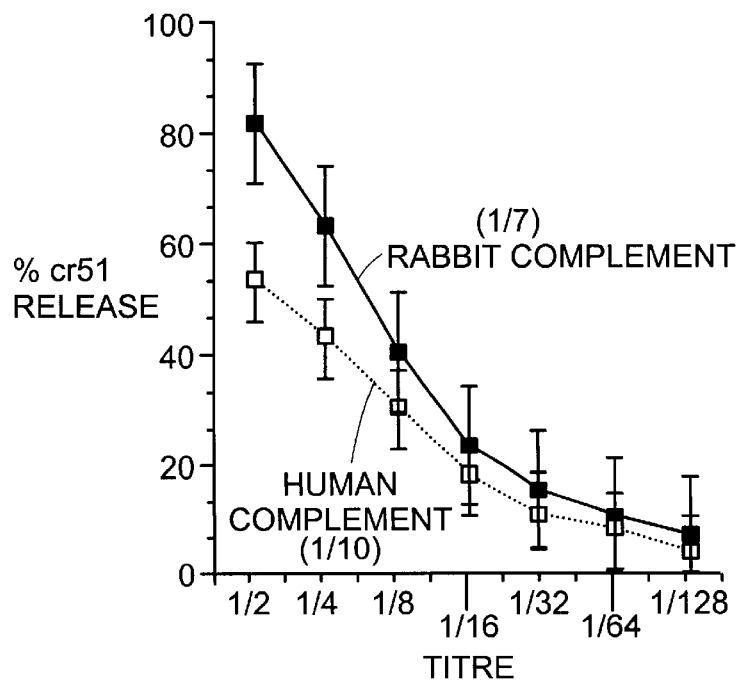
Figure 13:
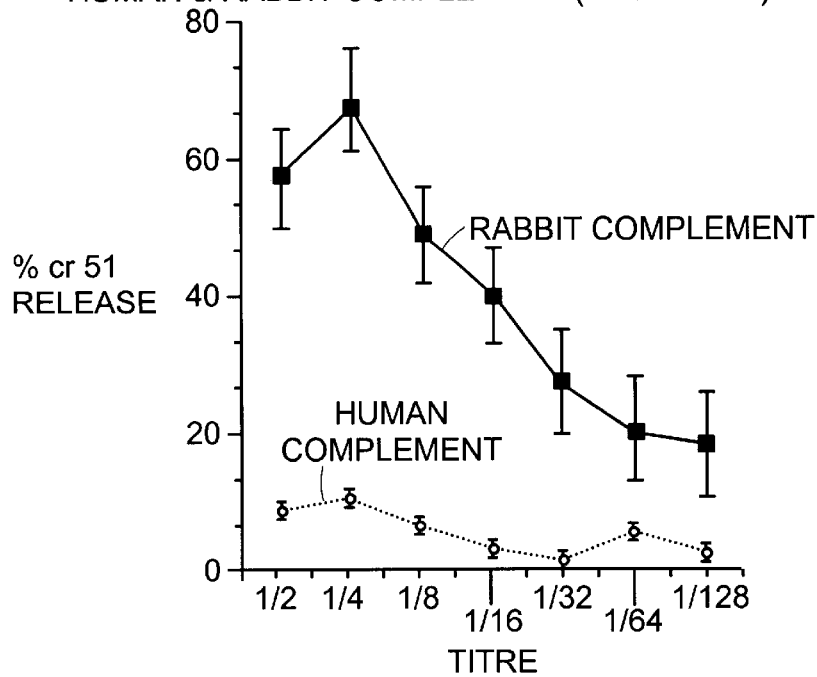
Figure 14:
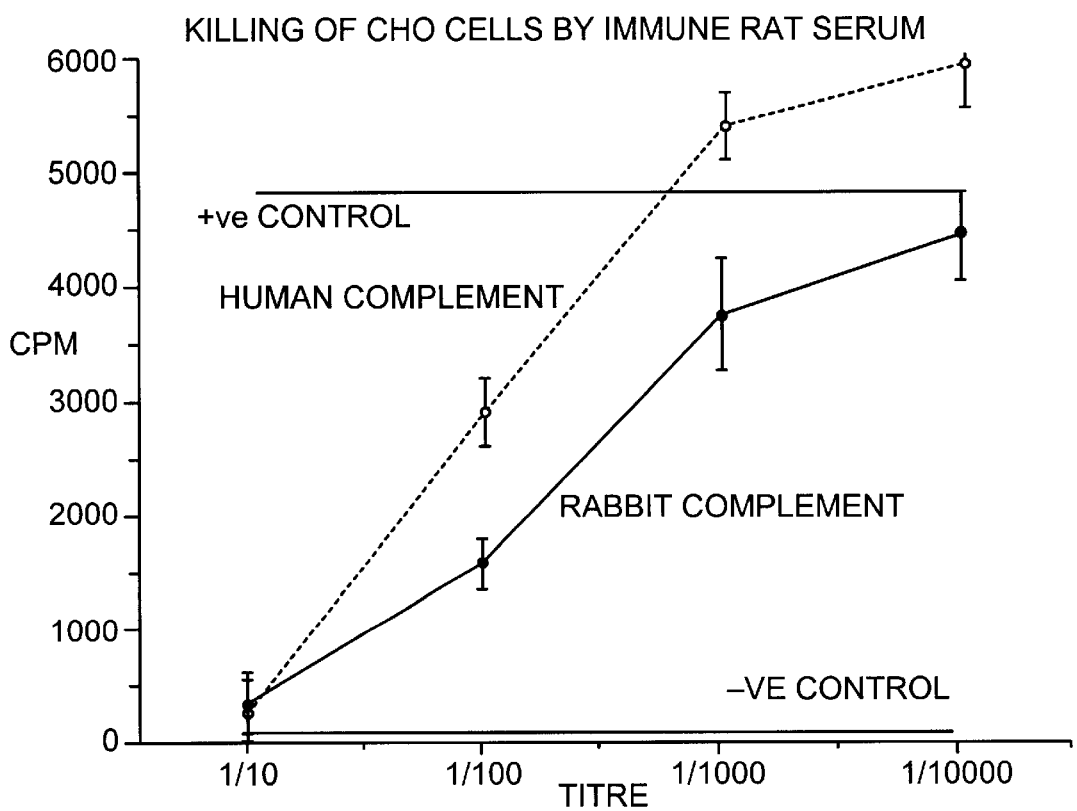
Figure 15:
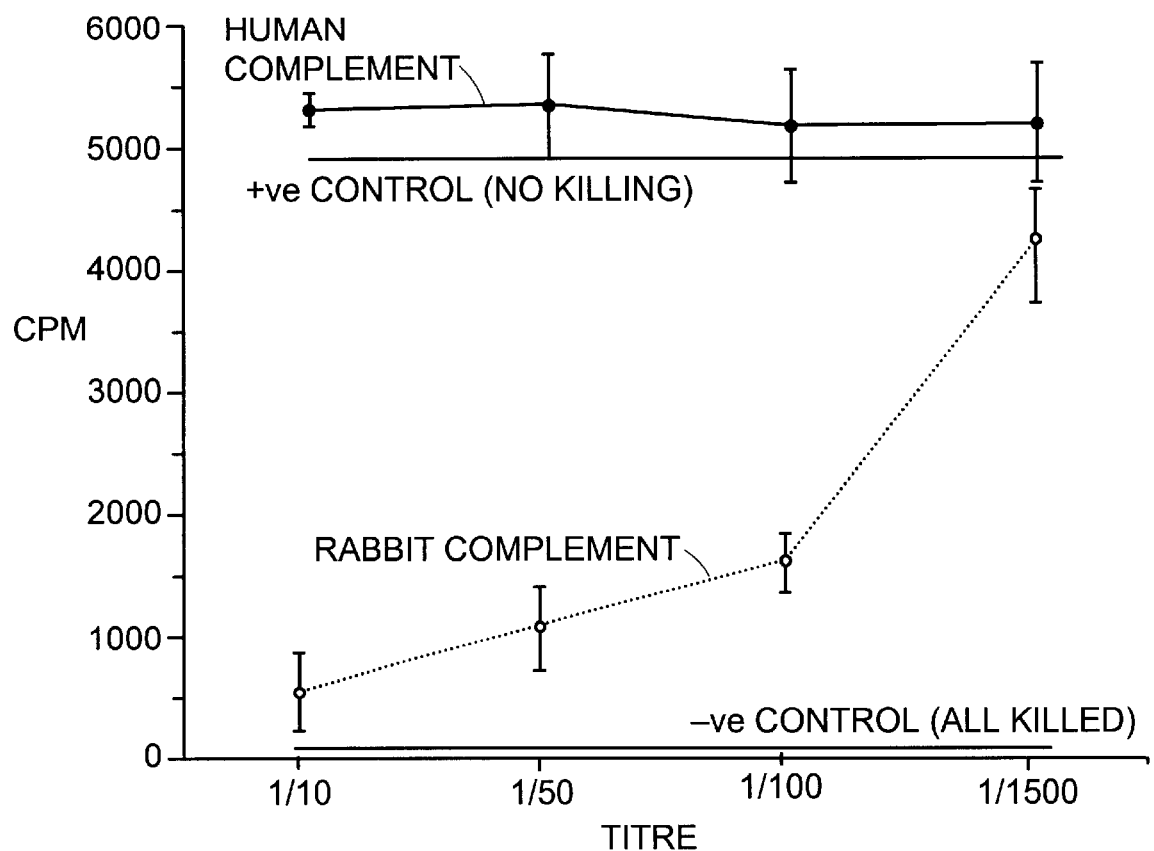
Figure 16:
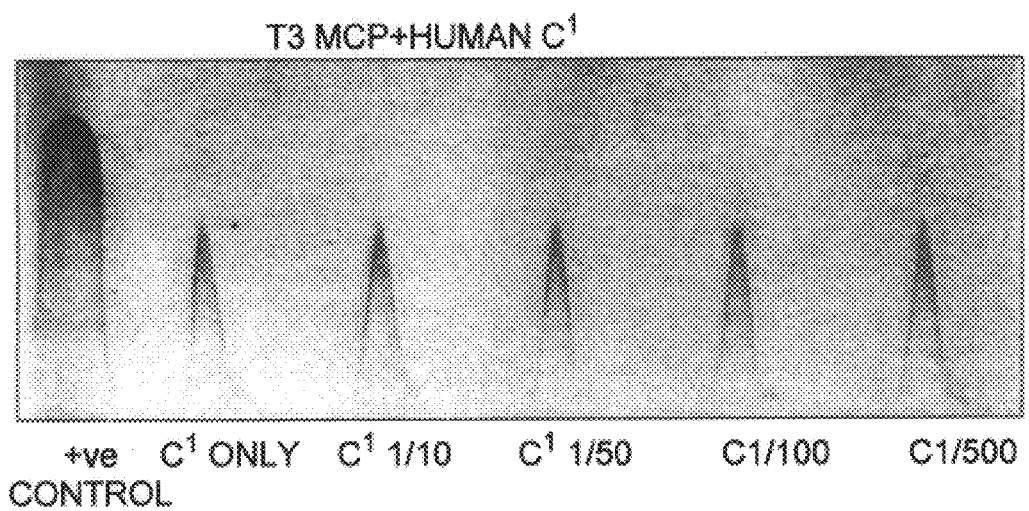
Figure 17:
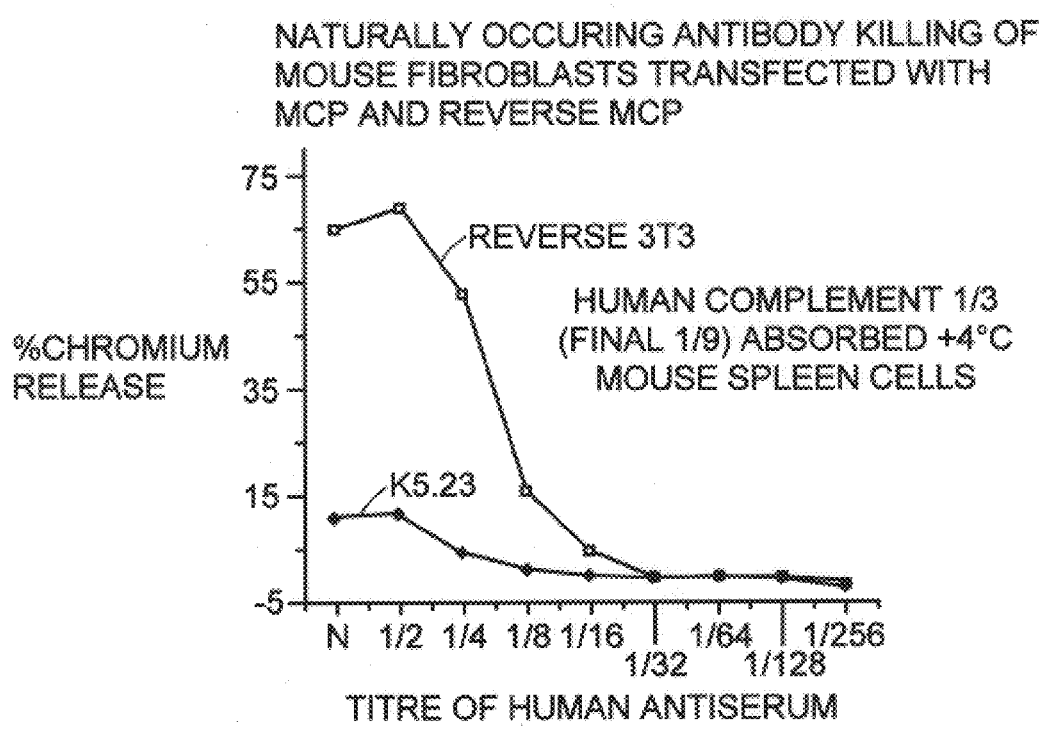
Figure 18:
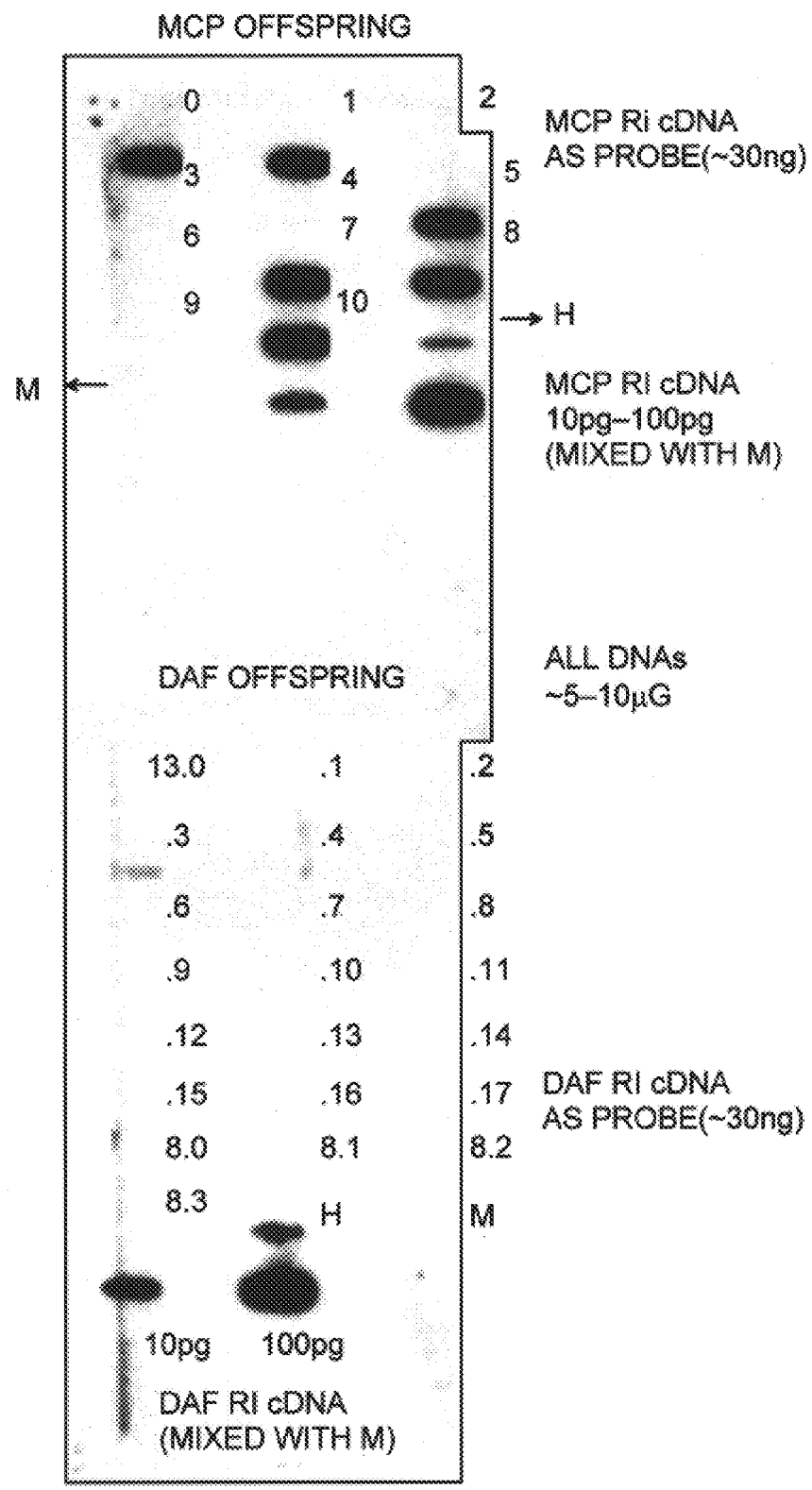

FIG. 7 illustrates titres of lytic anti-hamster antibodies from a rat recipient of a hamster heart graft, pre-transplant (day 0) and days 5, 7 and 9 post-transplant, as described in Example 6;

FIG. 8 shows graphically ODs of G200 fractions; the histogram illustrates titres in each fraction of lytic anti-hamster antibodies from a rat recipient of a hamster heart, as described in Example 6;

FIG. 9 shows a Southern blot of DNA extracted from T5, b10 and DB3 cell lines, as described in Example 7;

FIG. 10 shows $^{51}$Cr release figures, indicative of T5 human cell line being lysed by rabbit complement but not human complement in the presence of pig anti-human antibodies, as decscribed in Example 7;

FIG. 11 shows release figures, indicative of a failure of human antibodies to lyse T5 human cell line either with human or rabbit complement, as described in Example 7;

FIG. 12 shows $^{51}$Cr release figures, which demonstrate that human antibodies can lyse a mouse-mouse hybridoma (DB3) in the presence of both rabbit complement or human complement, as described in Example 7;

FIG. 13 shows $^{51}$Cr release, illustrating that the human-mouse hybrid cell line B10 is lysed by human antibodies in the presnce of rabbit complement but not lysed by human antibodies in the presence of human complement, as described in Example 7;

FIG. 14 shows uptake of $^{3}$H adenine (in counts per minute) by CHO cells, showing that these cells are killed by immune rat serum in the presence of human complement or rabbit complement, as described in Example 8;

FIG. 15 shows uptake of $^{3}$H adenine in counts per minute by CHO cells transfected with human MCP, showing that these cells are killed by immune rat serum in the presence of rabbit complement but are not killed by this immune rat serum in the presence of human complement, as described in Example 8;

FIG. 16 shows "2D rockets" showing that, in the circumstances described in relation to FIG. 15, the C3 component of human complement is not cleaved to form C3b, as described in Example 8;

FIG. 17 shows $^{51}$Cr release figures, indicative of 3T3 mouse fibroblasts being lysed by naturally occurring antibodies in the presence of human complement and the protective effect of the expression of human MCP by the mouse cells; and FIG. 18 shows a slot blot analysis of DNA of second generation transgenic mice using labelled MCP cDNA (upper) or labelled DAF cDNA as a probe.

EXAMPLE 1

Xenograft Rejection Takes Place in the Absence of any Antispecies Antibodies

In general, animals cannot survive without circulating immunoglobulins. These are produced by lymphocytes in response to antigenic stimuli. In early neonatal life, however, passively transferred maternal immunoglobulin acts as a temporary substitute for this self-produced antibody. This passively transferred immunoglobulin confers protection on the young while early immune experience is acquired. In mammals this passive transfer of maternal immunoglobulin usually occurs both transplacentally and via colostrum. In a few species, however, the structure of the placenta is such that no maternal antibody can be transferred by this route. The pig is one such species. All maternal antibody is obtained from colostrum. Thus, new born pre-suckled pigs are in principle immunoglobulin-free.

Large white pigs were taken at birth and placed in a wooden cage warmed by hot-water bottles without being allowed to suckle. Two pigs from each farrowing were taken for each experiment. These animals weighed approximately 1 kg at the time of birth.

Baby New Zealand white rabbits weighing approximately 300 gms were used as donors. These donors were anaesthetised with hypnol and diazepam, the chest was opened and a vena cava cannulated by means of a 19 gauge needle. Cold (+4° C.) cardioplegia (Thomas No. 2) was infused until the heart stopped beating and had become perfused with cardioplegia. Cooling was also applied externally with cold cardioplegia directly from a syringe. The rabbits heart was then removed using standard surgical techniques and stored in cardioplegia solution at +4° C. until required. It has been found necessary to take these precautions because the rabbit heart proved to be highly susceptible to ischaemic damage.

Recipient pigs were anaesthetised initially by Halothane/O2 inhalation. An intravenous butterfly (23 gauge) needle was then inserted into a mammary vein, anaesthesia maintained by intravenous ketamine. The pig was simultaneously kept hydrated with intravenous saline. Serum and EDTA blood samples were drawn pre-transplant.

The rabbit heart was grafted into the neck of the pigs after the method of Heron (*Acta Pathol. Microbiol. Scand.* 79 366–372 (1971)). The aorta was anastomised end to side (6–0 prolene) to the carotid artery and the pulmonary artery anastomised to the jugular vein. All other cardiac vessels were ligated. Hearts began beating within a few minutes of removal of clamps. Heart rate was monitored throughout by a diascope/ECG monitor. The pig neck was not closed during the experiments, hearts were kept moist by covering with cling film.

Figure 1A:
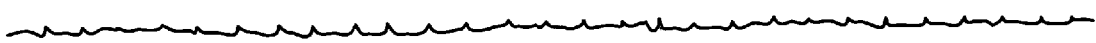
FIGS. 1A to 1E show successive ECG traces for a rabbit's heart grafted onto neonate pigs in accordance with Example 1.
Figure 1B:
Figure 1C:
Figure 1D:
Figure 1E:

The ECG results are shown in FIGS. 1A to 1E. The trace shown in FIG. 1A shows a normal heart beat immediately after transplantation. Failure begins some twenty minutes later (FIG. 1B) and within an hour (FIG. 1D) there is no detectable heart beat, evidencing hyperacute rejection.

This example therefore demonstrates that hyperacute rejection of discordant xenograft takes place even in the absence of antibodies.

EXAMPLE 2

The Neonatal Pigs used in Example 1 have no Antispecies Antibody

Rabbit anti-pig IgG was radioiodinated by the method of Greenwood et al, *Biochemical Journal* 89 114–123 (1963) modified by Davies and Howard (not published).

The following are added into a polystyrene tube (LP2 6 cm×1 cm) in rapid succession:

25–50 μl protein (at 1 mg/ml conc)

3–4 μl Na$^{125}$I (100 mCi/ml)

10 μl chloramine-T (*4 mg/5 ml; 0.5M)

sodium phosphate buffer (pH 7.5)

* must be freshly prepared before use

These components were allowed to mix for 30 seconds with continuous agitation. Then the following were quickly added:

50 μl DL-tyrosine (sat. sol. in 0.5 ml sodium phosphate buffer pH 7.5).

300 μl 2% BSA/PBS/azide

The labelled protein is then separated from the unreacted iodine, by the use of a small column 8cm×1.0 cm of Sephadex G-25 medium grade made up in PBS/azide. The iodination reaction mixture is quantitatively transferred to the prepared G25 column and eluted with PBS/azide. Six drop fractions are collected into polystyrene tubes (LP2). The column is eluted until both the protein and the ($^{125}$I) iodide peaks have been eluted and the radioactivity in all of the fractions is measured.

The radioactivity incorporated into the protein can be calculated thus:

radioactive counts in protein=original total counts−counts in iodide peaks

The radiolabelled IgG (referred to now as "isotope") is then used in an assay for (pig) antibodies in the neonatal pig, as follows:

Materials

PBS+0.01% Azide—Oxoid

PBS/BSA 1%—BSA-Sigma

Isotope—rabbit anti-pig IgG whole molecule with 12–18×103 counts/min.

Heat inactivated sera (56° C. 30 mins)

Anticoagulated blood samples.

Method

1. A 1% suspension of rabbit red blood cells in PBS was prepared and 100 μl amounts were added to tubes. Cells are spun to a button discarding supernatant.
2. Serial dilutions of inactivated sera were prepared in PBS/BSA from adult pig (positive control), neonatal pig (test sample) or rabbit (negative control). 0.025 ml amounts were added to red cell buttons in duplicate. Tubes were incubated at 4° C. for 4 hours.
3. After incubation tubes were washed three times in PBS/BSA 0.05 ml of Isotope was then added to each tube and incubated overnight at 4° C.
4. Tubes were rewashed three times and 1 min counts were performed on gamma counter.
5. Results are plotted as number of counts/min against titre.

Figure 2:
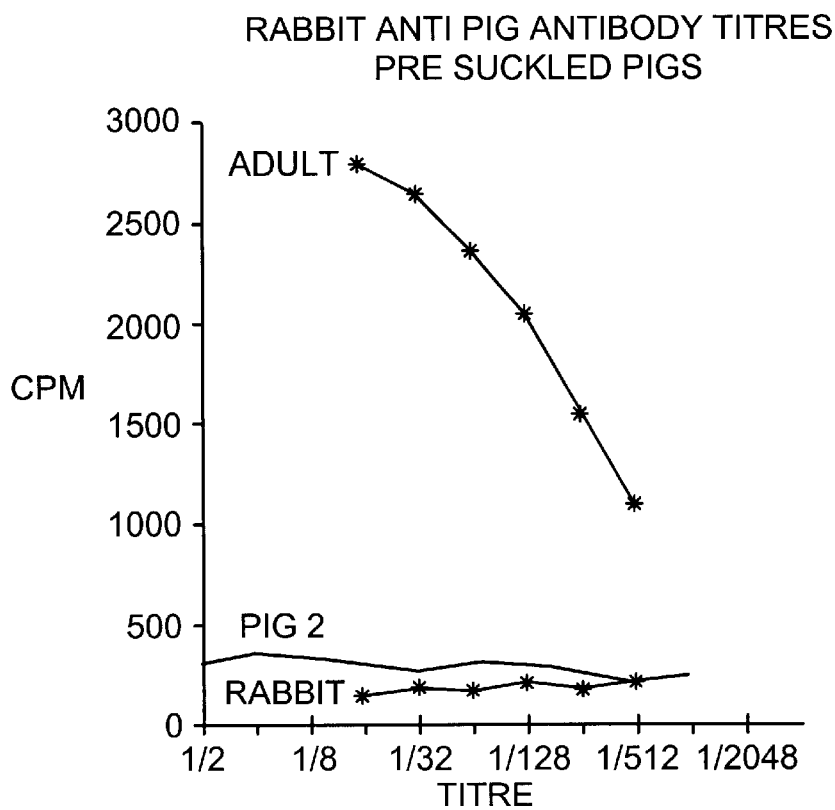
FIG. 2 shows the result of a radioimmunoassay indicating that the pigs used in Example 1 had no significant amounts of antispecies antibody.

The results are shown in FIG. 2. Rabbit serum was used as a negative control and adult (ie suckled) pig serum as a positive control. It can be seen that the level of pig antibody in the pre-suckled pig 2 is comparable to that of the negative control.

EXAMPLE 3

Demonstration of Relevance of Complement C3 to Xenoaraft Destruction

Complement deficient guinea pigs derived from the strain described by Burger et al (*Eur. J. Immunol* 16 7–11 (1986)) were grafted with hearts using essentially the same technique as that described for the rabbit-to-pig xenografts in Example 1. Rats were anaesthetised with ether inhalation and hearts cooled with cardioplegia and excised as previously described.

Guinea pig donors were anaesthatised with intravenous valium and intramuscular hypnol. Hearts were implanted into the neck as previously described. For control guinea pigs, i.e. those with normal complement levels, graft rejection normally took place within a few minutes, thus making it unnecessary to close the neck. In experimental animals the neck was closed and hearts monitored by twice daily palpation. Normal ECGs were observed for several hours post surgery, indicating no hyperacute rejection.

EXAMPLE 4

Figure 3:
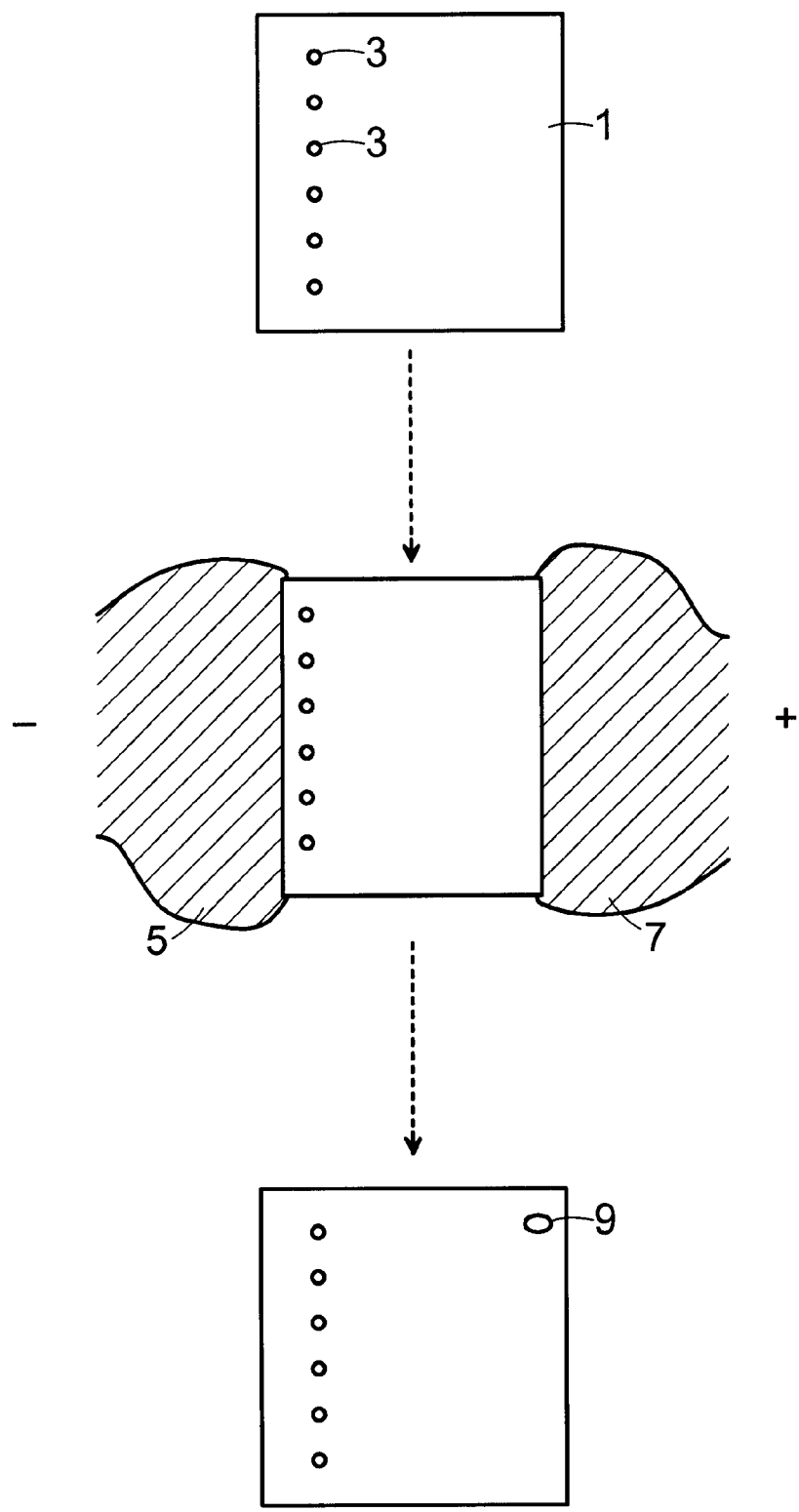
FIG. 3 shows certain stages of protein electrophoresis, as used in Example 4.

A. Pig Lymphocytes and Kidney Cells Activate Human Complement by the Alternative Pathway Following the technique of Grabar and Williams (*Biochim. Biophys. Acta* 10 193 (1953)), agarose gels 1 were poured onto 8×8 cm glass plates (FIG. 3). 10 ml of gel mixture was required, and this consisted of 5 ml 2% agarose and 5 ml veronal buffer (VB). (VB is 75 mM Na barbitone, 10 mM EDTA, 10 mM NaN$_3$, pH 8 5.) The agarose and VB were mixed together at 60° C. just before use. Gels were poured and cooled on a level platform. When set, the gel consisted of 1% agarose and had a depth of about 1.5 mm.

Wells 3 with a diameter of 3 mm were cut about 1 cm from one end of the gel. Each well could contain about 8 μl of the sample to be run. The sample had no special preparation apart from the addition of enough bromophenol blue to colour it. After application of the sample the gel was carefully placed onto the platform of the electrophoresis tank. Cotton wicks soaked in VB (the running buffer) were then gently pressed along the edge of the gel nearest tne wells, and another wick was pressed onto the opposite edge of the agarose. (It is important to ensure that the ends of the wicks dip into the buffer reservoirs.) A current of 25–30 mA was then passed through the gel until the albumin (visualised with bound bromophenol) reached the positive (anode) wick. The process takes about two and a half hours to three hours. If two or more gels are to be run simultaneously and in parallel then the current applied must be increased accordingly so that two gels required 50 mA and three require 75 mA, and so forth.

When electrophoresis was complete, as indicated by the travel of an albumen marker 9 visualised with bromophenol blue, the gel was removed from the electrophoresis tank.

B. 2-Dimensional Crossed Immunoelectrophoresis (2-D Rockets)

Figure 4:
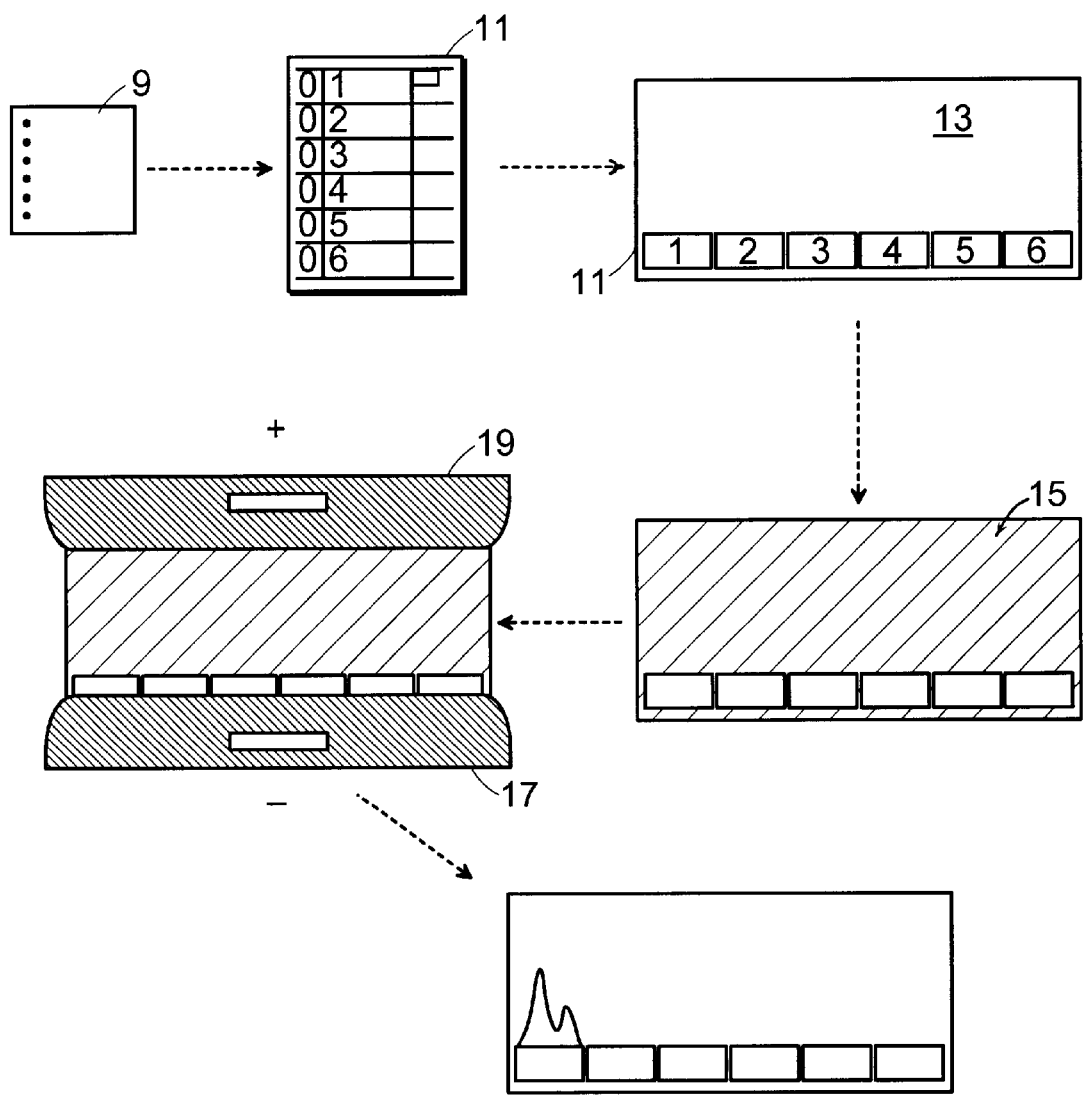
FIG. 4 shows certain stages of two dimensional crossed electrophoresis, as used in Example 4.

Strips 11 (FIG. 4) containing the electrophoresed proteins from (A), were cut and laid at one end of a new glass plate 13. A 1:1 mixture 15 of 2% agarose:VB containing about 1% antiserum to the protein to be visualised was then poured onto the plate and allowed to set. The antiserum was added to the agarose/VBS mixture when this had cooled to a temperature of about 50° C.

The rocket plate was then electrophoresed as described above, with the end of the gel containing the 1st dimension strips connected via a cotton wick to a negative electrode (cathode) 17 and the opposite end connected to an anode 19. The gels were electrophoresed overnight at a current dependent on the size of the gels; 10 mA is needed for each 8 cm length of gel so that a gel of 16 cm length requires 20 mA of current, and so forth.

The proteins are separated by the electrophoresis in the first dimension and quantified and visualised by electrophoresis in the second dimension, staining for the purpose of visualisation will now be described.

C. Squashing and Staining Gels

This procedure is the same for either conventional immunoelectrophoresis or rockets. The gel to be stained was covered with 1 layer of fibre-free POSTLIP™ paper (Adlard Evans & Co), pre-moistened with water. This was then covered with 6 layers of absorbent paper towelling. The assembly was squashed for 1 hour, after which all the paper was removed and the process repeated.

After the second squash the gel was dried under a current of warm air and then soaked in PBS for at least 1 hour to remove non-precipitated protein. The gel was then dried again, and stained for 10 minutes in a solution of 0.5% w/v coomasie brilliant blue G250, 45% $H_2O$, 45% methanol, 10% acetic acid.

The gel was de-stained by continuous washing in 20% methanol, 6% acetic acid until the background was clear. It was then finally dried under warm air.

Figure 5:
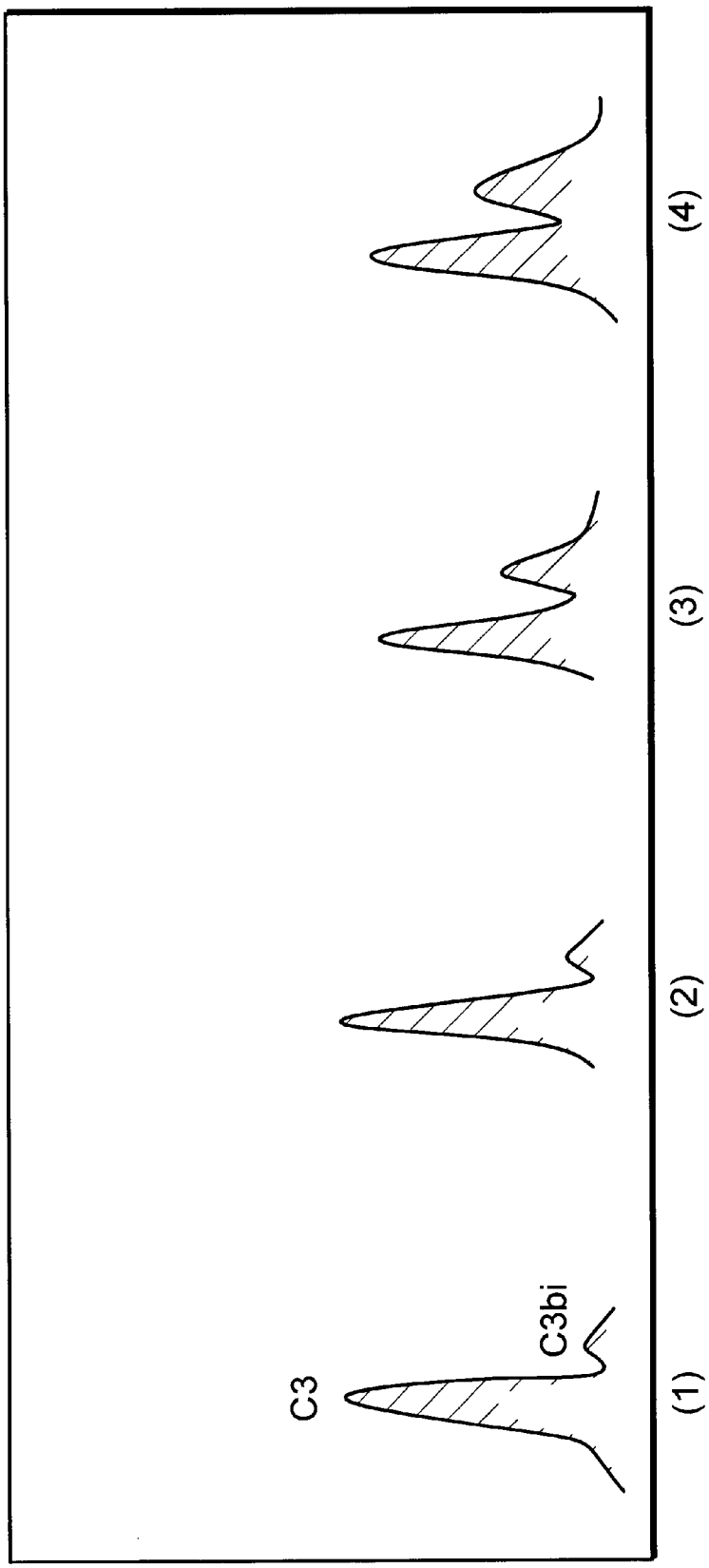
FIG. 5 shows the "2D-Rockets" resulting from Example 4.

FIG. 5 is a reproduction of the dry gel. Rocket 1 is a negative control containing 50 $\mu$l normal human serum (HHS) plus 25 $\mu$l VBS including 10 mM EGTA. EGTA is a chelator which removes calcium; calcium is essential for classical pathway complement activation, and so the presence of EGTA ensures that complement can only be activated by the alternative pathway. The left-hand (larger) peak is C3, and the right-hand (smaller) peak is C3bi, a breakdown product of activated C3. In the control, therefore, the small amount of C3bi indicates only a minor amount of complement activation.

In Rocket 2, 75% pig erythrocytes (v/v) were added to the buffer cocktail. There is a slight, but probably not significant, increase in the C3bi level, thereby indicating that pig erythrocytes only marginally, if at all, activate human complement by the alternative pathway. The reason for this poor response is not clear.

In Rockets 3 and 4, 75% pig lymphocytes (v/v) or 75% pig kidney cells (v/v), respectively, were added to the buffer cocktail. In each case there was an appreciable rise in the C3bi level, indicating activation of human complement by the pig lymphocytes.

EXAMPLE 5

Pig Lymphocytes are not Lysed by Human Antibodies in the Presence of Pig Complement, but are Lysed in the Presence of Rabbit or Human Complement A chromium release assay was used to monitor lysis of cells mediated by human serum in the presence of either pig complement, baby rabbit complement or human complement.

Materials
  Lymphocyte separation medium—Flowlabs
  RPMI 1640+10% inact. FCS
  PBS (without azide)—Oxoid
  V welled plates—Sterilin
  Baby rabbit comp lymph—Sera—lab—or human or pig complement (dilutes 1+7 in RPM1)
  Heat inactivate sera (56° C. 30 mins)

Method

1. Defibrinated whole pig blood, diluted 1:1 in PBS was layered onto an equal volume of Ficoll Hypaque lymphocyte separation medium. The tubes were spun at 1200 g for 30 mins at 20° C.
2. The resulting pig lymphocytes at the interface were removed and washed once in PBS. The button was resuspended in RPM1 1640 and the cell count is adjusted to $2 \times 10^7$/ml.
3. 200 $\mu$Ci of $^{51}$Cr were added to a $2 \times 10^7$ pellet of cells and incubated at room temperature for 1.5 hours.
4. Labelled cells were washed twice at 900 g for 5 min uses and adjusted to give a final cell count of $1 \times 10^6$/ml in RPM1.
5. 0.05 ml amounts of inactivated sera under test as serial dilutions in duplicate, together with controls, were plated out. Diluted complement was added to relevant wells in 0.05 ml amounts followed by 0.05 ml of labelled cells. Plates are incubated for 1 hour at 30° C. in a $CO_2$ oven.
6. After incubation, the plates were spun for 15 mins at 900 g 20° C. to sediment the cells. 100 $\mu$l of supernatant is removed into labelled tubes and 1 minute counts are performed on gamma counter.
7. Results are plotted as a % of the count of the original labelled cells against titre.

Controls
  Full release control (FRC)—50 $\mu$ls cells+100 $\mu$ls $H_2O$+0.1%+Tween
  Negative control—50 $\mu$ls cells+100 $\mu$ls RPM1
  Complement control (CC)—50 $\mu$ls cells+50 $\mu$ls dil'd. comp.+50 $\mu$ls RPM1 at the graft tissue and because of the further difficulty that the HCRF may have to be repeatedly administered to the recipient after the graft has taken place; however, this could be overcome by the use of specialist pharmaceutical delivery systems.

It will generally be much more convenient to provide the HCRF in such a way that it is integrated with the cell membrane on donor tissue. Although there may be some benign infections of the transplanted tissue which could cause suitable expression, by far the most preferred route of achieving this end is for the donor tissue to be transgenic in that it contains and expresses nucleic acid coding for one or more HCRFs active in the recipient species when grafted into the recipient. Such transgenic tissue may continue to express an HCRF indefinitely. The HCRF may be genetically derived from the recipient species or less preferably from a closely related species for which concordant xenografts may be possible.

Although in principle the transgenic donor tissue may come from a cell culture, it is preferable for the donor tissue to come from a transgenic animal. The transgenic animal should express (or be capable of expressing) the HCRF in at least the tissue to be transplanted, for preference. However, even this is not essential, as it may be possible to bind the HCRF to the cell membranes of the donor tissue by some binding agent (such as a hybrid monoclonal antibody (Milstein & Cuello *Nature* 305 537 (1983)) or receptor.

Results

Figure 6:
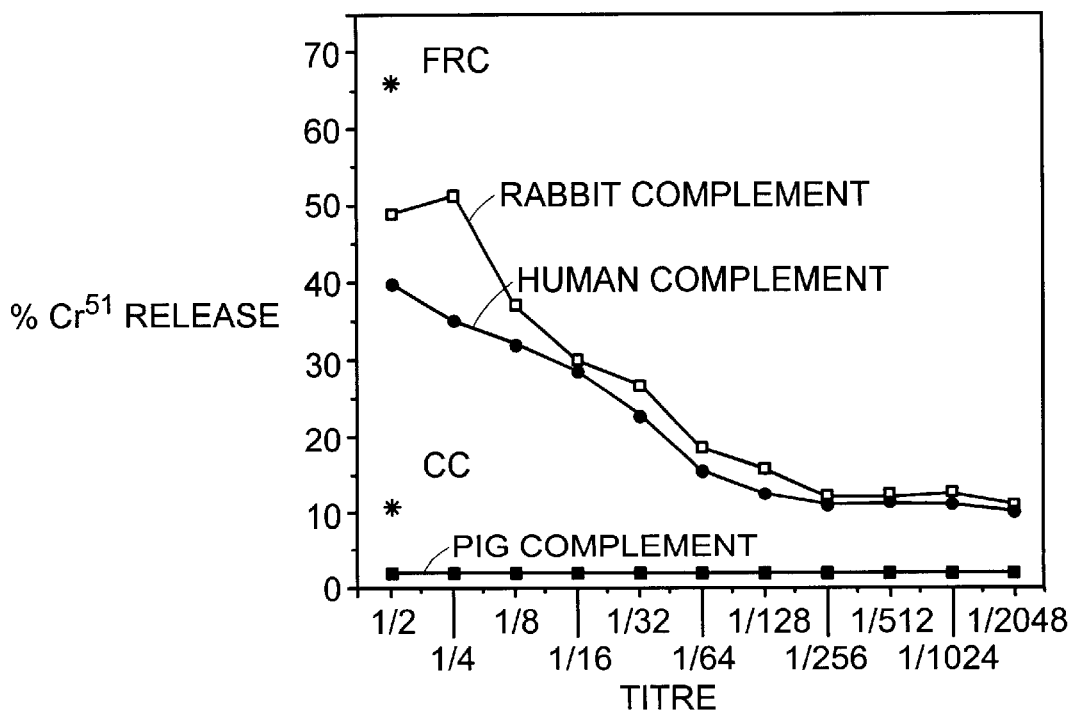
FIG. 6 shows the result of a chromium release cell lysis assay in Example 5.

The results are shown in FIG. 6. It can be seen that pig lymphocytes are lysed by human serum only in the presence of non-pig (ie rabbit or human) complement, but not in the presence of pig complement. The inference is that one or more homologous complement restriction factors present on pig cells successfully down-regulate the action of pig complement but not the action of human or rabbit complement.

EXAMPLE 6

The purpose of this example is to demonstrate that antibody can cause hyperacute rejection. The concept upon which this application is based arose as a result of the observation that hyperacute rejection may take place in the absence of anti-graft antibodies but requires functional complement. Because this is a novel observation there are no experiments in the literature which formally demonstrate that antibody can cause xenograft rejection. Since in the presence if naturally occurring antibody it is difficult to determine whether these antibodies are playing a role or not such an experiment is not easy to perform. In this example the role of antibody has been demonstrated by turning a concordant xenograft into a discordant xenograft by infusion of antibody of appropriate specificity. Recipients used in this study were male rats of the PVG strain (RT1C) (Banting & Kingdom, Bicester, Oxon., UK) between 3 and 6 months old weighing 250–300 g. Heart donors were Syrian hamsters also obtained from Banting & Kingdom and weighing between 100 and 150 g. Heart grafting was performed according to the method of Heron (loc. cit. in Example 1). Hamster hearts were grafted into the neck of the rats joining the aorta to the carotid artery and the pulmonary artery to the jugular vein by means of a cuff technique. All other vessels were ligated. Hearts started beating minutes after the release of vascular clamps and were monitored by external palpation. All operations were carried out on animals anaesthetised by inhalation of halothane and oxygen.

Anti-hamster lytic antibody levels were measured as follows: 50 μl of 1% hamster erythrocyte solution were added to 50 μl of test serum which had been diluted serially. 50 μl of a 1 in 7 dilution of baby rabbit complement (Sera Lab, Crawley Down, Sussex) were added and incubated for 1 hour at 37°C. 750 μl of complement fixation diluent were added and centrifuged (Beckman MICROFUGE, 13000 rpm for 4 minutes) after which the $OD_{415}$ was measured in the supernatant. (The word MICROFUGE is a trade mark. ) Positive and negative controls were CFD and distilled water added to a 1% solution of cells respectively. The results of the $OD_{415}$ readings were plotted against the serum titration on the x-axis. As can be seen from FIG. 7, grafting a hamster heart into a rat results in the rat producing very high titres of lytic anti-hamster antibodies. Sera from some of these rats were separated into their component protein fractions by column chromatography on SEPHADEX G200 (Pharmacia GB Ltd, London) using standard column chromatography techniques ("The use of SEPHADEX in the separation, purification and characterisation of biological materials", Curling in *Exp. in Physiol. and Biochem.* 3 (1970) 417–484 (G. A. Kerkut, Ed.) Academic Press, London and New York, 1970). (The word SEPHADEX is a trade mark. ) Each of the 7 ml fractions collected from the column were assayed for lytic anti-hamster activity as described above. FIG. 8 demonstrates that despite the fact that these antibodies were induced as a result of heart grafting the anti-species activity resides almost exclusively in the IgM fraction. After assaying for activity, fractions were concentrated using CX10 ultrafilters (Pharmacia) to a concentration of 0.5 mg/ml and stored at −70° C. until used.

To test for their ability to destroy a xenograft as opposed to just lysing red cells, hamster hearts were grafted into the necks of naive rats. As soon as the hamster heart beat was established either 2 ml of neat serum or 0.5 mg of purified immunoglobulin containing lytic anti-hamster antibodies were infused intravenously into the rat. Both the unseparated serum and the 0.5 mg of IgM consistently caused the hamster heart graft to be destroyed within 15 minutes. Results from infusion of IgG were inconsistent with some preparations causing the graft to fail while, in others, the graft continued to beat. When albumin from the G200 column was infused as a control heart grafts always survived and were rejected in the normal time for this model which is 3 days. This demonstrates that the binding of this antibody to a graft can induce its hyperacute destruction.

EXAMPLE 7

The data so far presented in this application have demonstrated that the destruction of a xenograft can involve complement activation either by the alternative pathway or by antibody-mediated complement activation (the classical pathway). Furthermore, complement regulators on the surface of the xenograft target can protect it from destruction by homologous but not heterologous complement. The critical activation step common to both complement activation pathways is the cleavage of the complement component C3. This cleavage is brought about by the C3 convertase, C4b2a (the classical pathway C3 convertase) or the convertase is C3bBb (the alternative pathway C3 convertase). These enzymes cleave C3 to C3b which, in turn, can engage the alternative pathway to form more C3 convertases (the feedback loop). As a result the complement system is rapidly able to amplify the deposition of C3b on a "foreign" target. Much of the C3b however does not successfully interact with the foreign target and remains in the fluid phase and can thus indiscriminately bind to the cells of the host. In order to protect these cells from attack by the indiscriminate binding of complement, control proteins have evolved to inactivate-complement components either in the fluid phase or bound to self tissues. Those glycoproteins which are involved in controlling C3 are genetically all associated within one region of human chromosome 1 called the RCA (regulators of complement activation) locus. In this example we demonstrate that mouse cells which have acquired through fusion techniques the human chromosome 1 and express proteins of the RCA locus an their surface behave in an in vitro assay of xenograft destruction as though they were human cells and not mouse cells.

Cell Lines

T5 is an Epstein Barr virus-transformed tonsil B-cell line produced by the technique of Bird et al. (*Nature* 289 300–301 (1981)). B10 is a human anti-tetanus monoclonal antibody producing hybridoma which was derived from the fusion of a human B lymphoblastoid line (BLL) with the mouse myeloma cell line X63-AG8.653 (Kierney et al. (*J. Immunol,* 123 1548–1550 (1979)). T5 and B10 cell lines are obtainable from Ms C Carter and Dr N C Hughes-Jones of the MRC MITI Group at Babraham, Cambridge. DB3 is a mouse hybridoma cell line which produces anti-progesterone monoclonal antibody (Wright et al. *Nature* 295 415–417 (1982)). The following oligonucleotide primers specific for human chromosome 1 were procured: (5'-CCACAGGTGTAACATTGTGT-3') [SEQ ID NO: 1] and (5'-GAGATAGTGTGATCTGAGGC-3') [SEQ ID NO: 2]; these are, respectively, upstream and downstream primers of human antithrombin 2 (AT3) gene known to be on human chromosome 1 (Wu et al. *Nucl. Acids Res.* 17 6433 (1989)). The oligonucleotides can be synthesised by techniques well known to those skilled in the art.

High molecular weight genomic DNA was prepared using the method of Herrmann and Frischauf (*Methods Enzymol.* 152 180–183 (1987)). In brief, 100×10$^6$ cells from each cultured cell line were lysed by 5 ml of TNE (100 mM Tris pH 7.5, 100 mM NaCl, 10 mM EDTA 1% Sarkosyl) and treated with fresh proteinase K (100 micrograms per ml). The preparation was extracted with phenol (water saturated and equilibrated against 0.1 M Tris, pH 8) phenol chloroform (1:1, V/V) and then chloroform isoamyl alcohol (24:1 V/V). DNA was obtained by ethanol precipitation and dialysed against TE (10 mM Tris pH8.0, 1 mM EDTA) made to 100 mM in NaCl and TE alone at 4° C. Isolated DNA was analysed on 0.5% agarose gel and the concentration determined by optical density at 260 nm. The polymerase chain reaction (PCR) for each cell line was performed as described by Saiki et al. (*Science* 239 487–491 (1988)). In a volume of 100 µl containing 500 ng of genomic DNA 1.2 ng of each primer and 2.5 units of Tag DNA polymerase (*Thermos acguaticus* type 3) (Cambio Ltd, Cambridge, UK) using the buffer supplied with the enzyme. The nucleotides (dNTPs) (Boehringer Mannheim Diagnostics and Biochemicals Ltd, Lewis, East Sussex, UK) were at a concentration of 2 mM each. DNA was amplfied for 30 cycles using a programmable thermal controller (Genetic Research Instrumentation Ltd, Dunmow, Essex, UK): denaturing 93° C. 1 minute: annealing 55° C. 1 minute: and extension 72° C. 2 minutes. 10 µl of the reaction product were analysed directly on a 2% agarose gel run in Tris boric acid EDTA buffer. The product size was determined by comparison with HincII digested phage X-174-rf DNA (Pharmacia LKB Biotechnology, Upsala, Sweden).

Cultured T5, B10 and DB3 cells were treated with anti-DAF (decay accelerating factor) monoclonal antibody (Kinoshita et al ((*J. Exp. Med.* 162 75–92 1985)) and fluoroscein-conjugated second antibody. Cells (1×10$^6$) were reacted with mouse anti-DAF monoclonal antibody 1A10 (IgG2a 10 µg/ml in 100 µl of 10% FCS 0.1% azide). 1A10 (Kinoshita ea al. (*J. Immunol.* 136 3390–3395 (1986))) was obtained from Dr M Davitz of New York University Medical Centre, New York USA. Blank controls were buffer alone. After incubation for 2 hours on ice the cells were washed 3 times, re-suspended and incubated in 100 µl buffer containing 1 in 100 FITC-conjugated goat F(ab')2 anti-mouse IG (heavy and light chains affinity purified and human IG absorbed) (Tago Immunochemicals Inc, Burlingame, Calif., USA) for one hour on ice. Some cells were incubated only with the second antibody as staining controls. Since DB3 is a mouse IgG1-secreting cell line, FITC-conjugated sheep anti-mouse IgG2A (1 in 40, The Binding Site Ltd, Birmingham, UK) or the goat anti-mouse IG preabsorbed with equal volumes of DB3 cells were also used in order to eliminate anti-IgG1 reactivity occurring when staining DB3 cells. All the cells were extensively washed and resuspended in 200 µl of buffer. DAF positive cells were detected using a Beckton Dickinson FACS-STAR apparatus for fluorescence-activated cell sorting (FACS) analysis. (The expression FACS-STAR is a trade mark.)

The PCR method was used to determine the presence of human chromosome 1 in three different cultured cell lines, T5 (human), B10 (human-mouse) and DB3 (mouse-mouse). FIG. 9 shows that after amplification both T5 and B10 had a band size of 495 base pairs whereas DB3 (ie the mouse-mouse hybrid) had no band at all. It has been reported that PCR products using AT3 primers consisted of 2 alleles, sized 572 base pairs (allele 1) and 496 base pairs (allele 2) (Wu et al., loc. cit.). The bands found in T5 and B10 genomic DNAs correspond to allele 2. This demonstrates that the human mouse hybrid cell line B10 contained human chromosome 1.

FACS analysis for the presence of DAF showed that the majority of the human T5 cells (85.7%) stained positive with anti-DAF monoclonal antibody. A similar level (83.1%) of positive cells was found in the mouse/human hybrid B10 cells. The mouse-mouse hyrbid DB3 cells showed identical staining patterns for both anti-DAF treated and untreated preparations. However, this anti-mouse IgG1 reactivity was removed if (1) FITC-conjugated sheep anti-mouse IgG2a was used or (2) the above goat anti-mouse IgG was preabsorbed with DB3 cells. The results indicate that human-mouse hybrid cell line B10 express human DAF on the cell membrane surface as detected by specific anti-DAF monoclonal antibodies. The level of expression is the same as for the human cell line T5. A mouse-mouse hybridoma cell line does not express human DAF.

Chromium release cytotoxic cell killing studies were performed on these cell lines as is described in Example 5 above. FIG. 10 shows that, when pig anti-human antibodies are incubated with the T5 human cell line the addition of rabbit complement caused lysis whereas no lysis occurs when human complement is added because, of course, the T5 cell line will possess human HCRFs. This is confirmation of the results of Example 5. When human antibodies are used on the human cell line no lysis occurs either with human complement or with rabbit complement, showing there are no auto-antibodies. The chromium release technique does not allow for incubations to be continued long enough to detect any signficiant levels of alternative pathway activation of the rabbit complement by the human cells (FIG. 11). However, when human antibodies are incubated with the DB3 mouse-mouse hybridoma cell line (FIG. 12), cell killing is achieved by both rabbit complement and human complement demonstrating that indeed human complement can function in such an assay. When the B10 human-mouse hybrid, possessing human chromosome 1 and known to be expressing at least DAF, was used then rabbit complement caused lysis of the cell line whereas human complement fails to cause lysis of the cell line (FIG. 13). The explanation for this is that the human HCRFs being expressed by virtue of possession of chromosome 1 on the mouse-human hybrid have inhibited the activity of the human complement.

EXAMPLE 8

The preceding example demonstrates that possession of chromosome 1 can prevent xenograft cell destruction. While this is strong circumstantial evidence that it is the CRA locus which is protecting the mouse cell from xenograft destruction this example provides formal proof. In this example, the effect of transfecting non-human cell lines with human MCP and exposing them to human or rabbit complement is demonstrated.

cDNAs were produced for MCP as described in detail by Lublin et al. (*J. Exp. Med.* 168 181–194 (1988)). Construction of transfected cell lines was performed using the expression plasmid SFFV.neo using the technique described by uhlbrigge et al. (*Proc. Natl. Acad. Sci.* 85 5649–5653 (1988). This contains the Friend spleen focus forming virus 5'long terminal repeat (SFFV.LTR) (Clark and Mak (*Nucl. Acids Res.* 10 3315–3330 (1982)) and (*Proc. Natl. Acad. Sci.* 80 5037–5041 (1983))). Cell lines were obtained from the American Type Culture Collection 12301 Parklawn Drive, Rockville, Md., USA. Cell lines used were CHO-K1 (ATCC CCL 61) and NIH/3T3 (ATCC CRL 1658). Expression of the gene was confirmed using a monoclonal antibody to MCP (Andrews et al. *Ann. Hum. Genet.* 49 31–39 (1985)) and FACS analysis as already described. In some cases cell lines were selected for high level expression of MCP by cell sorting on the FACS using standard techniques.

This example illustrates the effect of transfecting CHO cells with MCP. Because these cell lines grow as monolayers, cell killing was assessed by the terminal adenine uptake assay as descibred by de Bono et al. (*Immunology* 32 221–226 (1977)). In brief, this assay involved incubation of cell cultures in flat-bottomed sterile 96 well plates with complement and antibody. At the end of the experimental incubation period, cell viability is assessed by the ability of the culture to take up radioactive adenine. Viable cells will take up the adenine, dead cells will not; thus viable cells have high counts, dead cells have low counts.

In common with many transformed cells, CHO is insensitive to naturally occurring antibodies and the action of the alternative pathway of complement. However, these cells are sensitive to those antibodies which as has been demonstrated cause hamster heart xenograft destruction as described in Example 6. Since CHO cells are derived from hamster, these antibodies killed the CHO cells with both human and rabbit complement (FIG. 14). When CHO cells are transfected with human MCP, the cells can only be lysed in the presence of rabbit complement. Human complement has been inhibited by the presence of the human MCP on the surface of the hamster cell line (FIG. 15). Evidence that the failure of the cells to be killed is indeed due to a failure of C3 convertase is provided by analysis of the breakdown of the human C3 after incubation of the CHO cells by rocket immuno-electrophoresis as descibred in Example 4 above. As can be seen, no breakdown occurs above complement only control levels (FIG. 16).

These data confirm that genetically engineering complement down-regulatory proteins on the surface of non-human cells will protect those cells from the mechanisms of hyperacute xenograft destruction which have, as a common feature, a requirement for the cleavage of the C3 component of complement.

EXAMPLE 9

Following the procedure of Example 8, 3T3 mouse fibroblast cells were transfected with cDNA coding for MCP (MCP clone K5.23). $^{51}$Cr was added to the cells as described in Example 5. One volume of cells was then incubated with one volume of human heat-inactivated complement and one volume of human complement pre-absorbed at 4° C. with mouse spleen cells to remove anti-mouse antibody from the human complement. The mixture and serial dilutions with complement were plated out. General conditions and features of the chromium release assay are as described in Example 5. The results for clone K5.23 are shown in FIG. 17, which also shows, as a control, the effect of the MCP cDNA being introduced in the reverse orientation (in which case it is not transcribed). Correctly transcribed MCP cDNA confers protection on the cells from killing, as evidenced by the relatively low level of $^{51}$Cr release, whereas non-transcribed cDNA does not confer significant protection, as evidenced by the relatively high level of $^{51}$Cr release.

EXAMPLE 10

Similar results to those described in Example 8 above can be obtained with L1/210 cells (a mouse leukaemic cell line) transfected with with the CDNA for DAF. cDNAs were produced for DAF as described in Lublin & Atkinson (*Ann. Rev. Immunol.* 7 35–58 (1989)).

EXAMPLE 11 cDNA for MCP was prepared and ligated into SFFV.neo, as in Example 8 above.

Using this DNA preparation transgenic mice were produced as described in Manipulating the Mouse Embryo, A Laboratory Manual by B. Hogan et al, Cold Spring Harbour Laboratory (1986). Ten to fifteen (CBAxB10)f1 female mice, 3–4 weeks old, were induced to superovulate by intraperitonal injection of 5 units serum gonadotrophin from pregnant mares (supplied commercially as Folligon) followed 48 hours later by intraperitonal injection of 5 units chorionic gonadotrophin from human pregnancy urine (supplied commercially as Chorulon). The females were put to mate, on the day of the Chorulon injection, with (CBAxB10)F1 males and the next day females with vaginal plugs were killed by cervical dislocation and fertilized ova were isolated from their oviducts.

Three to four hundred ova, isolated in this way, contained two pronuclei clearly visible under Nomarski differential interference contrast optics at 400× magnification. One of the two pronuclei was injected with approximately 2000 copies of the DNA preparation containing the MCP cDNA transgene in concentrations ranging from 0.5 to 2 ng/μl.

Ova that survived the microinjection were reimplanted into the oviducts of (CBAxB10)F1 females that had mated the previous night with vasectomized males and were therefore pseudopregnant (ie, they had ovulated and their hormonal state was that of pregnancy but their own oocytes had not been fertilized). Approximately 30 microinjected ova were transferred to the oviducts of each pseudopregnant female, under anaesthesia, either on the same day of microinjection or the next day when the ova were at the 2-cell stage. Normal gestation ensued and seventeen mice were born from ten mothers. Screening of the offspring was done by slot blot and/or Southern blot (see Example 8), and also PCR, analysis of DNA from tail skin cells, utilizing $^{32}P$-labelled probes and primers that recognize the transgene. One of the offspring, a male, proved to be transgenic for the MCP DNA sequence.

EXAMPLE 12

The procedure of Example 11 was repeated, except that the cDNA for DAF, as described in Example 10, was used in place of the cDNA for MCP. Twenty three offspring were born from ten mothers. Three of them (two female, one male), transgenic for DAF, were obtained, as shown by Southern blotting.

EXAMPLE 13

The male mouse obtained in Example 11, containing a human MCP cDNA transgene was allowed to grow to maturity and mated with a (CBAxB10)F1 female. Eleven offspring resulted. Tail cell DNA from each offspring was screened by slot-blot analysis, using labelled human MCP cDNA as a probe, to determine whether the transgene had been inherited. The results are shown in the upper part of FIG. 18. It can be seen that offspring 0, 1, 5, 7, 8 and 10 have inherited. (Four controls were undertaken: human DNA (H); mouse DNA (M); mouse DNA mixed with 10 pg human MCP labelled cDNA; and mouse DNA mixed with 100 pg human MCP labelled cDNA.)

EXAMPLE 14

The male mouse obtained in Example 12, containing a human DAF CDNA transgene was allowed to grow to maturity and mated with a (CBAxB10)F1 female. For each of the resulting offspring, tail cell DNA was screened by slot-blot analysis, using labelled human DAF cDNA as a probe, to determine whether the transgene had been inherited. The results are shown in the lower part of FIG. 18. It can be seen that offspring 13.3 (a female) has inherited. (Four controls were undertaken: human DNA (H); mouse DNA (M); mouse DNA mixed with 10 pg human DAF labelled cDNA; and mouse DNA mixed with 100 pg human DAF labelled cDNA.)

2. The method as claimed in claim 1, wherein the HCRF has the activity of a natural HCRF whose gene is located in the RCA (regulator of complement activation locus mapping to band q32 of chromosome 1.

3. The method as claimed in claim 1, wherein the HCRF has the activity of decay accelerating factor (DAF).

4. The method as claimed in claim 1, wherein the HCRF has the activity of membrane cofactor protein (MCP).

5. A method of transplanting non-human donor tissue into a recipient mammal, wherein the donor tissue is from a non-human mammal of a different species from the recipient, the donor species being a discordant species with respect to the recipient, the method comprising grafting the donor tissue into the recipient, wherein said donor tissue is

What is claimed is:

1. A method of transplanting non-human donor tissue into a recipient mammal, wherein the donor tissue is from a non-human mammal of a different species from the recipient, the donor species being a discordant species with respect to the recipient, the method comprising grafting the donor tissue into the recipient, wherein said donor tissue is from a transgenic non-human mammal comprising transplantable tissue and whose genome comprises a DNA sequence or DNA sequences coding for a peptide or peptides having complement inhibiting activity of one or more homologous complement restriction factors (HCRFs) and said DNA sequence or DNA sequences are expressed in at least some of the cells of said tissue, wherein expression of said DNA sequence, or DNA sequences, results in transplantable tissue which inhibits complement mediated xenograft rejection on transplantation into or exposure to a component or components of the immune system of a discordant species.

from a transgenic non-human mammal comprising transplantable tissue and whose genome comprises a DNA sequence or DNA sequences coding for a peptide or peptides having complement inhibiting activity of decay accelerating factor (DAF) and said DNA sequence or DNA sequences are expressed in at least some of the cells of said tissue, wherein expression of said DNA sequence, or DNA sequences, results in transplantable tissue which inhibits complement mediated xenograft rejection on transplantation into or exposure to a component or components of the immune system of a discordant species.

6. A method of transplanting non-human donor tissue into a recipient mammal, wherein the non-human donor tissue is from a non-human mammal of a different species from the recipient, the donor species being a discordant species with respect to the recipient, the method comprising grafting the donor tissue into the recipient, wherein said donor tissue is from a non-human transgenic mammal comprising transplantable tissue and whose genome comprises a DNA sequence or DNA sequences coding for a peptide or peptides having complement inhibiting activity of membrane cofactor protein (MCP) and said said DNA sequence or DNA sequences are expressed in at least some of the cells of said tissue, wherein expression of said DNA sequence, or DNA sequences, results in transplantable tissue which inhibits complement mediated xenograft rejection on transplantation into or exposure to a component or components of the immune system of a discordant species.

7. The method as claimed in any of claim 1, 5 or 6, wherein the tissue is an organ.

8. The method as claimed in claim 7, wherein the organ is a heart, lung, liver, kidney, pancreas, thyroid, cornea, or skin.

9. The method as claimed in any of claim 1, 5 or 6, wherein the tissue comprises blood or haematopoietic cells, Islets of Langerhans, brain cells, or cells from endocrine organs.

10. A method of transplanting donor tissue of a transgenic pig into a recipient mammal of discordant species, the method comprising grafting the donor tissue of the transgenic pig into the recipient mammal of discordant species,
   wherein said donor tissue comprises transplantable tissue, and wherein the genome of said transgenic pig comprises DNA encoding a peptide or peptides having complement inhibiting activity of one or more homologous complement restriction factors and said DNA is expressed in at least some of the cells of said donor tissue,
   wherein expression of said DNA results in transplantable tissue which inhibits complement-mediated xenograft rejection when said donor tissue is transplanted into the recipient mammal of discordant species or exposed to a component or components of the immune system of a discordant mammal species.

11. A method according to claim 10 wherein the recipient mammal of discordant species is a primate.

12. A method according to claim 10 wherein the DNA encodes a peptide or peptides having complement inhibiting activity at the C3 stage.

13. A method according to claim 10 wherein the DNA encodes a peptide or peptides having complement inhibiting activity of one or more homologous complement restriction factors selected from MCP and DAF.

14. A method according to claim 10 wherein the DNA encodes a peptide or peptides having complement inhibiting activity of the homologous complement restriction factor DAF.

15. A method according to claim 10 wherein the DNA encodes a peptide or peptides having complement inhibiting activity of the homologous complement restriction factor MCP.

16. A method of transplanting donor tissue of a transgenic pig into a human recipient, the method comprising grafting transplantable tissue of the transgenic pig into the human recipient,
   wherein the genome of said transgenic pig comprises DNA encoding a peptide or peptides having complement inhibiting activity of one or more homologous complement restriction factors and said DNA is expressed in at least some of the cells of said donor tissue,
   wherein expression of said DNA results in transplantable tissue which inhibits complement-mediated xenograft rejection when said donor tissue is transplanted into the human recipient or exposed to a component or components of the immune system of a human.

17. A method according to claim 16 wherein the DNA encodes a peptide or peptides having complement inhibiting activity of one or more homologous complement restriction factors selected from MCP and DAF.

18. A method according to claim 16 wherein the DNA encodes a peptide or peptides having complement inhibiting activity of DAF.

19. A method according to claim 16 wherein the DNA encodes a peptide or peptides having complement inhibiting activity of human DAF.

20. A method according to claim 16 wherein the DNA encodes a peptide or peptides having complement inhibiting activity of MCP.

21. A method according to claim 16 wherein the DNA encodes a peptide or peptides having complement inhibiting activity of human MCP.

22. A method of transplanting donor tissue of a transgenic pig into a human recipient, the method comprising grafting transplantable tissue of the transgenic pig into the human recipient,
   wherein the genome of said transgenic pig comprises DNA encoding a human homologous complement restriction factor consisting essentially of DAF, said DNA being expressed in at least some of the cells of said donor tissue,
   wherein expression of said DNA results in transplantable tissue which inhibits complement-mediated xenograft rejection when said donor tissue is transplanted into the human recipient or exposed to a component or components of the immune system of a human.

23. A method according to claim 22 wherein the DNA comprises human DAF cDNA.

24. A method according to claim 10, 16 or 22 wherein the tissue is an organ.

25. A method according to claim 24 wherein the organ is a heart, lung, 'r liver, kidney, pancreas, thyroid, cornea, or skin.

26. A method according to claim 10, 16 or 22 wherein the tissue comprises blood or haematopoietic cells, Islets of Langerhans, brain cells, or cells from endocrine organs.

27. The method as claimed in claim 10, 16 or 22 wherein the HCRF has the activity of a natural HCRF whose gene is located in the RCA (regulator of complement activation locus mapping to band q32 of chromosome 1.

28. A method of transplanting donor tissue of a transgenic mouse into a recipient mammal of discordant species, the method comprising grafting the donor tissue of the transgenic mouse into the recipient mammal,
   wherein said donor tissue comprises transplantable tissue, and
   wherein the genome of said transgenic mouse comprises DNA encoding a peptide or peptides having complement inhibiting activity of one or more homologous complement restriction factors, said DNA being expressed in at least some of the cells of the donor tissue,
   wherein expression of said DNA results in transplantable tissue that inhibits complement-mediated xenograft rejection when said tissue is transplanted into the recipient mammal of discordant species or exposed to a component or components of the immune system of a discordant species.

29. A method according to claim 28 wherein the homologous complement restriction factors are selected from DAF and MCP.

* * * * *

UNITED STATES PATENT AND TRADEMARK OFFICE
CERTIFICATE OF CORRECTION

PATENT NO. : 6,482,404 B1
DATED : November 19, 2002
INVENTOR(S) : White et al.

It is certified that error appears in the above-identified patent and that said Letters Patent is hereby corrected as shown below:

Title page,
Insert Items:
-- [30]  Foreign Application Priority Data
  Aug. 06, 1990   (UK) ................... 9017198
  Oct. 12, 1989   (UK) ................... 8922987  --; and
-- [63] Related U.S. Application Data
Continuation of application no. 08/347,210, filed November 21, 1994, now U.S. Patent No. 6,495,735 B1, which is a continuation of application no. 07/839,755, filed June 9, 1992, now abandoned, which is a 371 of PCT/GB90/01575, filed October 12, 1990. --

Signed and Sealed this

Twenty-seventh Day of July, 2004

JON W. DUDAS
*Acting Director of the United States Patent and Trademark Office*